US012600692B2

(12) United States Patent
Lee et al.

(10) Patent No.: US 12,600,692 B2
(45) Date of Patent: Apr. 14, 2026

(54) PRODUCTION AND PURIFICATION OF ACETIC ACID

(71) Applicant: Celanese International Corporation, Irving, TX (US)

(72) Inventors: David Lee, Houston, TX (US); Yaw-Hwa Liu, Missouri City, TX (US); Ronald D. Shaver, Houston, TX (US)

(73) Assignee: Celanese International Corporation, Irving, TX (US)

( * ) Notice: Subject to any disclaimer, the term of this patent is extended or adjusted under 35 U.S.C. 154(b) by 642 days.

(21) Appl. No.: 17/928,567

(22) PCT Filed: Jun. 3, 2021

(86) PCT No.: PCT/US2021/035688
§ 371 (c)(1),
(2) Date: Nov. 29, 2022

(87) PCT Pub. No.: WO2021/247854
PCT Pub. Date: Dec. 9, 2021

(65) Prior Publication Data
US 2023/0202957 A1     Jun. 29, 2023

Related U.S. Application Data

(60) Provisional application No. 63/034,078, filed on Jun. 3, 2020.

(51) Int. Cl.
*C07C 51/12* (2006.01)
*C07C 51/44* (2006.01)

(52) U.S. Cl.
CPC .............. *C07C 51/12* (2013.01); *C07C 51/44* (2013.01)

(58) Field of Classification Search
CPC ......... C07C 51/12; C07C 51/44; C07C 51/47; C07C 53/08
See application file for complete search history.

(56) References Cited

U.S. PATENT DOCUMENTS

| | | | |
|---|---|---|---|
| 7,390,919 | B1 | 6/2008 | Salisbury et al. |
| 2010/0121101 | A1 | 5/2010 | Shaver |

(Continued)

FOREIGN PATENT DOCUMENTS

| | | |
|---|---|---|
| CN | 102224126 A | 10/2011 |
| CN | 102612506 A | 7/2012 |

(Continued)

OTHER PUBLICATIONS

International Search Report and Written Opinion for PCT/US2021/035688 mailed Sep. 21, 2021, all pages.

(Continued)

*Primary Examiner* — Deborah D Carr
(74) *Attorney, Agent, or Firm* — Kilpatrick Townsend & Stockton LLP

(57) ABSTRACT

Provided herein is a process for the production and purification of acetic acid. In particular, this disclosure relates to improved processes for producing and purifying acetic acid by the carbonylation of methanol in the presence of a Group VIII metal carbonylation catalyst. The acetic acid production and purification process described herein controls the formation and mass composition of acetal impurities, such as 1,1-dimethoxyethane.

20 Claims, 3 Drawing Sheets

(56) References Cited

U.S. PATENT DOCUMENTS

| | | | | |
|---|---|---|---|---|
| 2018/0118651 A1* | 5/2018 | Shimizu | .................. | B01D 3/40 |
| 2020/0140365 A1* | 5/2020 | Shaver | ................... | C07C 51/12 |

FOREIGN PATENT DOCUMENTS

| | | | |
|---|---|---|---|
| CN | 107001222 | A | 8/2017 |
| CN | 107709279 | A | 2/2018 |
| JP | 0812612 | A | 1/1996 |
| JP | 2011502145 | A | 1/2011 |
| JP | 2015526466 | A | 9/2015 |
| TW | 201229022 | A | 7/2012 |
| TW | 201332958 | A | 8/2013 |
| WO | 2013/070212 | A1 | 5/2013 |
| WO | 2016194850 | A1 | 12/2016 |

OTHER PUBLICATIONS

International Preliminary Report on Patentability for PCT/US2021/035688 issued Dec. 6, 2022, 9 pages.

Notification of the First Office Action for CN202180040032.2 dated Mar. 29, 2024, 15 pages.

Notification of the Second Office Action for CN202180040032.2 dated Aug. 5, 2024, 8 pages.

Application No. JP2022-574391 , Notice of Allowance, Mailed On Sep. 5, 2025, 3 pages.

MYPI2022006777 , "Substantive Examination Adverse Report", Aug. 29, 2025, 4 pages.

JP2022-574391, "Office Action", Dec. 26, 2024, 9 pages.

TW110120145, "Office Action", Mar. 6, 2025, 7 pages.

JP2022-574391, "Office Action", Jun. 2, 2025, 3 pages.

SG11202260750T, "Written Opinion", Jun. 13, 2025, 7 pages.

* cited by examiner

PRODUCTION AND PURIFICATION OF ACETIC ACID

PRIORITY

This application is a U.S. National Phase of PCT/US2021/035688, filed Jun. 3, 2021, entitled "LOW IMPURITY LIQUID STREAMS," which claims priority to U.S. Provisional Application No. 63/034,078, filed on Jun. 3, 2020, the entire contents of which are incorporated herein by reference for all purposes.

FIELD

This disclosure relates generally to a process for the production and purification of acetic acid. In particular, this disclosure relates to improved processes for producing and purifying acetic acid by the carbonylation of methanol in the presence of a Group VIII metal carbonylation catalyst. More specifically, this disclosure pertains to production and purification wherein the acetal impurities, such as 1,1-dimethoxyethane, are controlled.

BACKGROUND

The carbonylation process of methanol (acetic acid production by carbonylation of methanol) is known as a suitable industrial method for the production (synthesis) of acetic acid. In this process, for example, methanol is allowed to react continuously with carbon monoxide in the presence of a metal catalyst (catalyst system) in a reaction vessel (reactor). The reaction mixture is evaporated in an evaporator (e.g., flasher), and the flashed vapor portion is purified in a distillation column (referred to as a light ends column or splitter column) to remove lower boiling point components. The reaction mixture may then be further purified or treated in one or more subsequent distillation columns to yield a product acetic acid.

In the carbonylation process for producing acetic acid, other by-products (e.g., carbonyl impurities) are also formed during the reaction and/or subsequent purification steps. For example, acetaldehyde may be formed as a by-product (impurity). Furthermore, these by-products may undergo subsequent reactions to produce additional impurities. For example, crotonaldehyde may be produced by the aldol condensation of acetaldehyde, and 2-ethyl crotonaldehyde may be produced by the aldol condensation of crotonaldehyde. These by-products (impurities) reduce the quality of the product acetic acid, particularly by affecting the potassium permanganate test value of the product acetic acid. It is therefore desirable to reduce or remove the presence of these impurities from streams in the acetic acid carbonylation process.

Systems for reducing the concentration of acetaldehyde in the acetic acid carbonylation process are known and widely used in the industrial production of acetic acid. These systems typically include treating at least a portion of the overhead of the first distillation column, for example, by distillation, absorption, or combinations thereof, to separate acetaldehyde. In some cases, the overhead may be collected in a receiver and allowed to separate into phases (phase-separate). In particular, the overhead may be allowed to separate into phases, such as an upper phase and a lower phase. A portion of the upper phase and/or the lower phase may then be subjected to further treatment to separate and remove acetaldehyde.

Although existing carbonylation processes are highly efficient, further improvements for the recovery of acetic acid in a safe and efficient manner continue to be desirable.

SUMMARY

Embodiments of the present disclosure provide an industrial process for effectively and efficiently producing acetic acid having a good potassium permanganate test value.

Another embodiment of the present disclosure is to provide a method for effectively reducing the mass composition of 1,1-dimethoxyethane during the process for producing acetic acid. As used herein the terms "mass composition" or "concentration" refers to the mass fraction of substance to the total mass and is generally expressed in wt %, unless indicated otherwise.

Still another embodiment of the present disclosure is to provide a method for effectively preventing the oxidation of 1,1-dimethoxyethane during the process for producing acetic acid.

The present inventors conducted diligent and intensive studies to achieve the above objects; as a result of those studies, the following methods have been developed.

In one embodiment, there is provided a process for producing acetic acid, comprising (a) a reaction step of allowing methanol to continuously react with carbon monoxide in a reactor in the presence of a reactive system comprising a metal catalyst, an ionic metal iodide, and methyl iodide, acetic acid, methyl acetate, and water; (b) an evaporation step of separating a reaction mixture obtained in the reaction step with or without heating into a vapor stream and a liquid residuum stream; (c) a first distillation step of distilling at least a portion of the vapor stream in a first distillation column to form a first overhead stream and a side stream, wherein the first overhead stream comprises water, methyl iodide, and/or acetaldehyde, and the side stream comprises acetic acid; (d) a phase separation step of condensing the first overhead stream in one or more condensers, collecting the condensates in a receiver, and separating the condensates into an upper phase and a lower phase; (e) a second distillation step of distilling at least a portion of the lower phase in a second distillation column to form a second mixture comprising acetaldehyde; and (f) an acetaldehyde separation step of separating the second mixture into an acetaldehyde stream and a first return stream. The mass composition of 1,1-dimethoxyethane in a liquid stream of the process is controlled to be not more than 0.2 wt. %. The process may also comprise at least one step selected from the group consisting of (g) to (k): (g) a purifying step of purifying the side stream to obtain an acetic acid product stream; (h) an off-gas treatment step of absorbing one or more off-gas streams from the process with an absorption solvent and forming a carbon monoxide stream and a second return stream; (i) a high-boiler removal step of removing a higher boiling component from the acetic acid product stream; (j) an iodine removal step of contacting the acetic acid product stream with an ion-exchange resin and separating an iodine compound from the acetic acid product stream; and (k) an extraction step of extracting acetaldehyde from the acetaldehyde stream to form an extract and a raffinate, wherein the extract comprises acetaldehyde and the raffinate comprises methyl iodide; wherein the mass composition of 1,1-dimethoxyethane in a liquid stream of the process is controlled to be not more than 0.2 wt. %.

BRIEF DESCRIPTION OF THE DRAWINGS

The present invention will be better understood in view of the appended non-limiting figures, wherein.

Figure 1:
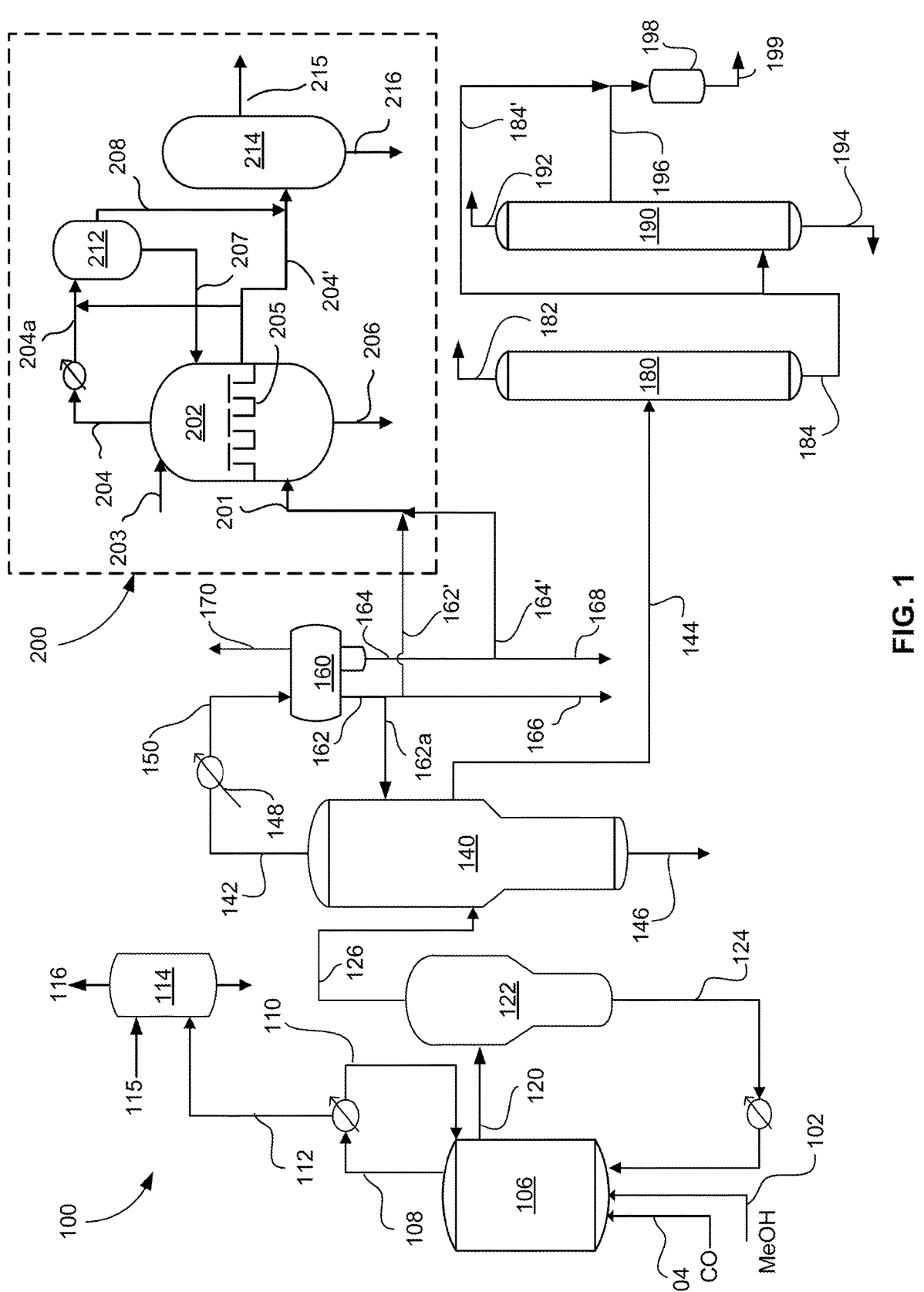
FIG. 1 illustrates a schematic of a process for the production and purification of acetic acid in accordance with embodiments of the present disclosure.

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

As is evident from the figures and text presented herein, a variety of embodiments are contemplated.

DETAILED DESCRIPTION

As discussed herein, the processes relate to continuous acetic acid production, and in particular acetic acid production processes that include one or more steps for removing and/or reducing acetaldehyde and other carbonyl impurities from the system. The present inventors have conducted diligent studies and have determined that other impurities may be present in the system. In particular, the present inventors have found that acetals, including 1,1-dimethoxyethane, may be present in various liquid streams in the acetic acid production and purification system. The inventors have found that 1,1-dimethoxyethane may enter a liquid stream by various factors, including by streams introduced to the process from the outside and/or by in situ formation, e.g., by the reaction of acetaldehyde and methanol. In one embodiment, the liquid stream may comprise methyl iodide, and has a mass ratio of methyl iodide to water that is greater than 1, e.g., greater than 3 or greater than 5.

The presence of 1,1-dimethoxyethane in the system presents a number of problems. As an impurity, 1,1-dimethoxyethane reduces the quality (purity) of the acetic acid product. Furthermore, the present inventors have found that 1,1-dimethoxyethane may react to form acetaldehyde. Increased amounts of acetaldehyde reduce the quality (purity) of the acetic acid product and acetaldehyde may undergo side reactions that produce other carbonyl impurities. The in situ formation of acetaldehyde thus negatively affects the quality of the acetic acid product as well as reduces the efficiency of systems for reducing and/or removing acetaldehyde from the system, e.g., by acetaldehyde removal systems.

A process for producing acetic acid (acetic acid production by carbonylation of methanol) according to one embodiment of the present disclosure comprises a reaction step of allowing methanol and/or a methanol derivative, such as methyl acetate, or dimethyl ether, to continuously react with carbon monoxide in a reactor (reaction vessel) in the presence of a reactive system (catalyst system) comprising a metal catalyst (e.g., rhodium or iridium catalyst), an ionic metal iodide, and methyl iodide, acetic acid, methyl acetate, and water; an evaporation step of separating a reaction mixture obtained in the reaction step with or without heating into a vapor stream and a liquid residuum stream; a first distillation step of distilling at least a portion of the vapor stream in a first distillation column (which may also be referred to as a splitter column or light ends column)

to form a first overhead stream and a side stream, wherein the first overhead stream comprises water, methyl iodide, and/or acetaldehyde, and the side stream comprises acetic acid; a phase separation step of condensing the first overhead stream in one or more condensers, collecting the condensates in a receiver, and separating the condensates into an upper phase (e.g., aqueous phase, or otherwise referred to as light phase) and a lower phase (e.g., organic phase, or otherwise referred to as heavy phase); a second distillation step of distilling at least a portion of the lower phase in a second distillation column to form a second mixture comprising acetaldehyde; an acetaldehyde separation step of separating the second mixture into an acetaldehyde stream and a first return stream; and wherein the mass composition of 1,1-dimethoxyethane in a liquid stream of the process is controlled and/or maintained to be not more than 0.2 wt. %. In addition to these steps, the process may include at least one step selected from the group consisting of: a purifying step of purifying the side stream to obtain an acetic acid product stream; an off-gas treatment step of absorbing one or more off-gas streams from the process with an absorption solvent and forming a carbon monoxide stream and a second return stream; a high-boiler removal step of removing a higher boiling component from the acetic acid product stream; an iodide removal step of contacting the acetic acid product stream with an ion-exchange resin and separating an iodide compound from the acetic acid product stream; and an extraction step of extracting acetaldehyde from the acetaldehyde stream to form an extract and a raffinate, wherein the extract comprises acetaldehyde and the raffinate comprises methyl iodide. It should be understood that the order of the purifying step, high-boiler removal step, iodine removal step, and/or ion-exchange resin may vary depending on the process and in some embodiments, these steps may be skipped.

According to one embodiment, the mass composition of 1,1-dimethoxyethane in a liquid stream of the process is controlled and/or maintained through the methanol mass composition. The inventors have found that the formation of acetals, in particular 1,1-dimethoxyethane, is due to a reversible reaction of methanol and acetaldehyde. Since the reaction can be manipulated to drive the reaction to completion with an excess (high amount) of reagent, the formation of 1,1-dimethoxyethane is driven by an excess (high amount) of methanol. Therefore, the 1,1-dimethoxyethane mass composition in a liquid stream can be limited or decreased by controlling the amount of methanol. In particular, because acetaldehyde may form 1,1-dimethoxyethane in the first distillation column, the mass composition of 1,1-dimethoxyethane can be decreased by controlling the amount of methanol in the vapor stream produced in the evaporation step. Furthermore, because acetaldehyde may form 1,1-dimethoxyethane in the second distillation column, the mass composition of 1,1-dimethoxyethane can be decreased by controlling the amount of methanol in the lower phase of the phase separation step.

According to another embodiment, the mass composition of 1,1-dimethoxyethane in a liquid stream of the process is controlled by regulating the residence time in the first distillation column and/or the second distillation column. As noted above, the inventors have found that 1,1-dimethoxyethane tends to form in one or both of these columns. In particular, the inventors have found that distillation time contributes to the formation of 1,1-dimethoxyethane. Therefore, the 1,1-dimethoxyethane mass composition in a liquid stream can be decreased by controlling the residence time. In particular, the mass composition of 1,1-dimethoxyethane can be decreased by controlling the residence time in the first distillation column (light ends column; splitter column) and/or the second distillation column. In these embodiments, the residence time in the first distillation column (light ends column, splitter column) and/or the second distillation column is, for example, not less than 1 minute, preferably not less than 2 minutes, or more preferably not less than 5 minutes. Because distillation step(s) is/are an important aspect of purification, it is important that the residence time not be so severely limited as to negatively impact the final purity of the product acetic acid.

In the embodiments of the present disclosure, the mass composition of 1,1-dimethoxyethane in a liquid stream is less than or equal to 0.2 wt. %, e.g., less than or equal to 0.15 wt. %, less than or equal to 0.1 wt. %, or less than or equal to 0.05 wt. %. In terms of ranges, the mass composition of 1,1-dimethoxyethane may be from 0.001 wt. % to 0.2 wt. %, e.g., from 0.01 to 0.2 wt. %, from 0.01 wt. % to 0.15 wt. %, from 0.01 wt. % to 0.1 wt. %, or from 0.01 wt. % to 0.05 wt. %.

Hereinafter, several embodiments of the present disclosure will be described. FIG. 1 is a flow diagram of a carbonylation process of methanol (acetic acid production by carbonylation of methanol) 100, according to one embodiment. This apparatus is configured to be capable of continuously producing acetic acid. An acetic acid production apparatus associated with this carbonylation process flow diagram includes a reactor (reaction vessel) 106, an evaporator 122, a first distillation column 140, a receiver 160, a second distillation column (202), and a third column 180. As shown and described herein, various liquid streams are generated by the process as described herein. Due to the higher methyl iodide content, most of these liquid streams are recycled to the reactor 106 and thus any impurities in these liquid streams tend to build up in the process. In particular, a liquid stream obtained from the residue (bottom stream) 206 of second distillation column is returned to reactor 106 may have a build-up of impurities and thus it is desirable to control or maintain the mass composition of 1,1-dimethoxyethane at a value of less than or equal to 0.2 wt. % in residue 206. In one embodiment, the liquid stream returned to the reactor has a mass ratio of methyl iodide to water that is greater than 1, e.g., greater than 3 or greater than 5. Further to prevent the formation of peroxides the liquid stream is not contacted with air.

As shown and described herein, the liquid stream may be any one of the liquid streams shown in FIG. 1, including a stream selected from the side stream, the condensates, the bottom streams, the upper phase, the lower phase, the second mixture, and/or the acetic acid product stream. In one embodiment, the liquid stream is a bottom or residue from a distillation column.

It should be understood to those skilled in the art that various processing equipment is not shown in detail in FIG. 1, including heat exchangers, receivers, pumps, controls, valves, etc. Unless stated otherwise, the absence of such processing equipment would be understood by one skilled in the art that such processing equipment would be used as appropriate.

Hereinafter, the embodiments will be explained in detail with reference to the figures as necessary. There is at least one corresponding unit for each step described in the various processes and may be referred to interchangeably.

Reaction Step

In the reaction step, methanol (methanol derivative) is allowed to continuously react with carbon monoxide in a reactor in the presence of a reactive system. For example, in the embodiment shown in FIG. 1, a methanol-containing feed (first reagent) stream 102 and a carbon monoxide-containing feed (second reagent) stream 104 are fed into a reactor (e.g., a liquid phase carbonylation reactor) 106, in which the carbonylation reaction occurs to form acetic acid. Although not shown, a flow transmitter may be present on the both feed streams to control and/or monitor the flow of each respective stream. In particular, controlling and/or monitoring the mass flow of the methanol-containing feed stream is useful for determining the efficiency of the process.

The methanol-containing feed stream 102 comprises methanol and/or at least one reactive derivative selected from the group consisting of methanol, dimethyl ether, and methyl acetate. The methanol-containing feed stream 102 may be derived in part from a fresh feed, a recycled stream from the system, or some combination thereof. At least some of the methanol and/or reactive derivative thereof will be converted to, and hence be present as, methyl acetate in the liquid medium by an esterification reaction with acetic acid. The unreacted methanol amount in reactor 106 may be less than or equal to 1 wt. % based on the total weight of the reaction mixture, e.g., less than or equal to 0.8 wt. %, less than 0.5 wt. %, or less than 0.3 wt. %.

The methanol-containing feed stream 102 may comprise 1,1-dimethoxyethane and may be a source of the impurity in the system. Preferably, the methanol-containing feed stream is substantially free of 1,1-dimethoxyethane. Depending on the source of the raw material, the methanol-containing feed stream may comprise very low amount of acetal, e.g., less than or equal to 0.2 wt. %, e.g., less than or equal to 0.0001 wt. % or less than or equal to 0.00005 wt. %. Because the methanol-containing feed stream may comprise 1,1-dimethoxyethane, and even at low amounts, it is preferred that streams containing oxygen, such as air, not be allowed to contact the methanol-containing feed stream, so as to reduce the risk of oxidation.

In one embodiment, the stream comprising 1,1-dimethoxyethane may be contacted with a sufficient amount of ozone to form methyl acetate. The methyl acetate can be used as a reactant to increase the production of acetic acid.

Carbon monoxide-containing feed stream 104 may comprise primarily carbon monoxide of greater than or equal to 95 vol. %, e.g., greater than or equal to 97 vol. % or greater than or equal to 99 vol. %. In some embodiments, minor impurities such as hydrogen, carbon dioxide, oxygen, and/or nitrogen may be present in amount of less than 5 vol. %, e.g., less than 3 vol. % or less than 1 vol. %. These minor impurities may also be generated by various side reactions under operating conditions.

Typical reaction temperatures for carbonylation are from 150 to 250° C., with the temperature range of 180 to 225° C. being a preferred range. The reaction pressure for carbonylation may be from 15 atm to 40 atm (absolute), with the pressure range of 20 to 35 atm (absolute) being preferred. The carbon monoxide partial pressure in the reactor can vary widely but is typically from 2 to 30 atm, e.g., from 3 to 10 atm. The hydrogen partial pressure in the reactor is typically from 0.3 to 2 atm, e.g., from 0.3 to 1.5 atm, or from 0.4 to 1.5 atm. These partial pressures can be maintained by known methods, including introducing carbon monoxide-containing stream or hydrogen-containing stream into the reactor, and/or by venting the reactor, e.g., via line 108. A portion of the vented stream line 108 may be condensed and returned to the reactor via line 110. The production rate of acetic acid may be from 5 to 50 mol/L·h, e.g., from 10 to 40 mol/L·h, and preferably 15 to 35 mol/L·h. "Greater production rates" generally refers to operating above 20 mol/L·h.

The reactor (liquid phase carbonylation reactor) 106 is preferably self-agitating (capable of agitation), for example, a mechanically stirred vessel, a vessel with educted or pump-around mixing, or bubble-column type vessel, with or without an agitator, within which the reacting liquid or slurry contents are maintained, preferably automatically, at a pre-determined level, which preferably remains substantially constant during normal operation. Into carbonylation reactor 106, fresh methanol, carbon monoxide, and sufficient water are continuously introduced as needed to maintain suitable mass compositions in the reaction mixture. Carbon monoxide is introduced at a rate sufficient to maintain the desired internal reactor pressure. In some embodiments, carbon monoxide is continuously introduced into the carbonylation reactor, desirably below the agitator, which may be used to stir the contents, and thoroughly disperse the carbon monoxide throughout the liquid reaction medium.

The material of the carbonylation reactor and its internals is not particularly limited and may be a metal, a ceramic, a glass, or combinations thereof. For example, the material may include zirconium-based materials and alloys that tend to have high corrosion resistance, but may also include iron-based alloys (stainless steel), nickel-based alloys (HASTELLOY™ or INCONEL™), titanium-based materials and alloys, or aluminum-based materials or alloys.

As noted above, the reaction system of the reaction step includes a metal catalyst. The metal catalyst (carbonylation catalyst) may comprise a Group VIII metal. Suitable Group VIII catalysts include cobalt, rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion. In one embodiment, the metal catalyst may be a homogenous catalyst. Other embodiments, may support the catalyst on a fixed bed, for example.

The reactive system also includes a catalyst co-promoter, such as an ionic metal iodide (iodide salts; salt co-promoter). These may be in the form of a soluble salt of an alkali metal or alkaline earth metal, quaternary ammonium, phosphonium salt or mixtures thereof. In certain embodiments, the catalyst co-promoter is lithium iodide, lithium acetate, and/or mixtures thereof. The ionic metal iodide may be added as a non-iodide salt that will generate an iodide salt. The iodide catalyst stabilizer may be introduced directly into the reaction system. Alternatively, the iodide salt may be generated in-situ since, under the operating conditions of the reaction system, a wide range of non-iodide salt precursors will react with methyl iodide or hydroiodic acid in the reaction mixture to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, which are incorporated herein by reference in their entirety. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entirety.

The reactive system also includes a halogen-containing catalyst promoter (co-promoter) of the catalyst system, such as a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The carbonylation reaction is an exothermic reaction that accompanies heat generation, and the reaction temperature may be controlled (or regulated) to maintain production levels. In view of the natures of the carbonylation reaction and temperature of the reactor may be regulated by a variety of methods. For purposes of the present disclosure, any suitable cooling may be used to regulate the temperature of the reactor. In one embodiment, temperature may be controlled by using a heat-removable (or heat-removing) unit or a cooling unit (e.g., a jacket), using a pump-around loop for cooling, recycling of the condensate which has been cooled or from which heat has been removed, or other means. A usable process to remove part of the reaction heat allows a vapor (vent gas) from the reactor to be cooled in a condenser, a heat exchanger, or other means to separate the vapor into liquid components and gaseous components, and the liquid components and/or the gaseous components may be recycled to the reactor. U.S. Pat. No. 5,374,774 describes a cooling unit in the recycle line for the reactor. A pump around loop may be used to generate additional heat for the production of steam while regulating the temperature of the carbonylation reactor, which is further described in U.S. Pat. No. 8,530,696. In some embodiments, the temperature of the reactor may be controlled by condensing a portion of the flash overhead that is returned to the reactor, which is further described in U.S. Pat. No. 8,957,248.

Returning to the reactor 106, the catalyst in the reaction medium plays the role of promoting the methanol carbonylation reaction. In commercial production, the metal catalyst does not activate methanol directly, so a more reactive methyl substrate (reactant) must be generated in situ. An iodide promoter, such as hydrogen iodide, converts the methanol into methyl iodide. However, since most of the reaction medium is acetic acid, the methanol is esterified to methyl acetate, which is activated by hydrogen iodide into methyl iodide.

The components of the reaction mixture are maintained within defined limits to ensure sufficient production of acetic acid. The reaction mixture contains a mass composition of the metal catalyst, e.g. rhodium catalyst, in an amount from 100 to 3000 wppm, e.g., from 400 to 2000 wppm, or from 400 to 1500 wppm as the metal, e.g., rhodium. The mass composition of water in the reaction mixture is maintained to be less than 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction mixture contains less than 4 wt. % water, e.g., less than 3.5 wt. %, less than 3 wt. %, or less than 2 wt. %. In terms of ranges, the reaction mixture contains 0.1 to 3.5 wt. % water, e.g., from 0.1 to 3 wt. % or from 0.5 to 2.8 wt. %. The mass composition of methyl iodide in the reaction mixture is maintained to be from 1 to 25 wt. %, e.g., from 5 to 20 wt. %, from 4 to 13.9 wt. %. The mass composition of iodide salt, e.g., lithium iodide, in the reaction mixture is maintained to be from 1 to 25 wt. %, e.g., from 2 to 20 wt. %, from 3 to 20 wt. %. The mass composition of methyl acetate in the reaction mixture is maintained to be from 0.5 to 30 wt. %, e.g., from 0.3 to 20 wt. %, from 0.6 to 4.1 wt. %. The following amounts are based on the total weight of the reaction mixture. The ranges disclosed in this application include the endpoints, sub-ranges and individual values. In a continuous process, the amounts of components are maintained within the ranges provided and fluctuations within these ranges are anticipated. One of ordinary skill would readily understand how to control the process to maintain the amounts of components in the reaction medium.

The mass composition of acetic acid in the reaction mixture is generally more than 30 wt. %, e.g. more than 40 wt. % or more than 50 wt. %.

In some embodiments, the desired reaction rates are obtained even at low water mass compositions by maintaining in the reaction mixture an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water conditions, methyl acetate and lithium iodide act as rate promoters only when relatively high mass compositions of each of these components are present and that the promotion is higher when both of these components are present simultaneously.

In one embodiment, the carbonylation reaction of methanol to acetic acid product is carried out by contacting the methanol feed with gaseous carbon monoxide (second reagent) bubbled through an acetic acid solvent reaction mixture containing the metal (rhodium) catalyst, MeI promoter, an ester of the methanol (methyl acetate), and additional soluble iodide salt, at conditions of temperature and pressure suitable to form the carbonylation product. It will be generally recognized that it is the mass composition of iodide ion in the catalyst system that is important and not the cation associated with the iodide, and that at a given molar mass composition of iodide the nature of the cation is not as significant as the effect of the iodide mass composition. Any metal iodide salt, or any iodide salt of any organic cation, or other cations such as those based on amine or phosphine compounds (optionally quaternary cations), can be maintained in the reaction mixture provided that the salt is sufficiently soluble in the reaction mixture to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002 March (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion mass composition is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

The reaction mixture (crude liquid mixture) may also contain impurities that should be controlled to avoid by-product formation. Examples of these components include ethyl iodide, formic acid, propionic acid, acetaldehyde, crotonaldehyde, 2-ethyl crotonaldehyde, and/or butyl acetate. Impurities present in the reaction mixture can be classified as lower boiling point impurities, which have a boiling point lower than that of acetic acid, and higher boiling point impurities, which have a boiling point higher than that of acetic acid. Examples of lower boiling point impurities include acetaldehyde, and crotonaldehyde; examples of higher boiling point impurities include propionic acid, butyl acetate, 2-ethyl crotonaldehyde and including mixtures thereof. There also may be gaseous components that are evolved during the various reactions (including but not limited to hydrogen, methane, and/or carbon dioxide).

These impurities have negative impacts on the quality (purity) of the acetic acid product. In addition, the byproducts and/or impurity formation is not limited to the reactor, and it may occur in a downstream treatment system such as a distillation column or receiver vessel. As noted above, for the purposes of the present disclosure the presence of 1,1-dimethoxyethane is particularly problematic and builds up when liquid streams have unacceptable high amounts. Although, 1,1-dimethoxyethane tends to favor to a greater extent in the downstream treatment system instead of the reactor, in some embodiments, the mass composition of 1,1-dimethoxyethane in the reaction mixture (e.g., liquid stream) may be maintained below 0.2 wt. % or less, e.g., less than or equal to 0.15 wt. %, less than or equal to 0.1 wt. %, or less than or equal to 0.05 wt. %.

Byproducts may be controlled by regulating the reaction medium and, in addition, the byproducts may be removed by separation process as described further herein. For example, as described in U.S. Pat. No. 8,017,802, formic acid may be controlled by the water content in the reactor and/or temperature of reactor resulting in a formic acid content in the acetic acid product that is less than 160 wppm, e.g., less than 140 wppm, or less than 100 wppm. Separation of byproducts may be limited by the associated costs. When the byproducts are not removed, especially higher boiling point components, the components can concentrate in the acetic acid product. Thus, it is useful to limit the production of byproducts in the reactor to reduce the need for separation. For example, in some embodiments, the propionic acid mass composition in the acetic acid product may further be maintained below 250 wppm by maintaining the ethyl iodide mass composition in the reaction medium at less than or equal to 750 wppm, e.g., less than or equal to 400 wppm, less than or equal to 350 wppm, or less than or equal to 300 wppm, without removing propionic acid from the acetic acid product.

In one embodiment, carbon monoxide is continuously introduced into the reactor (liquid phase carbonylation reactor), desirably below the agitator, which may be used to stir the contents (reacting liquid). The gaseous feed of carbon monoxide may be thoroughly dispersed through the contents (reacting liquid) by this stirring means. An off-gas (gaseous purge stream) 108 may be vented from the reactor 106 to prevent buildup of gaseous by-products and to maintain or control a carbon monoxide partial pressure at a given total reactor pressure. In one embodiment, the gaseous purge stream 108 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.6 wt. %, less than or equal to 0.5 wt. % and/or the gaseous stream comprises hydrogen iodide in an amount of greater than or equal to 0.001 wt. %, e.g., greater than or equal to 0.005 wt. %, greater than or equal to 0.01 wt. %, greater than or equal to 0.05 wt. %, greater than or equal to 0.1 wt. %. The temperature of the reactor may be controlled and the carbon monoxide feed is introduced at a rate sufficient to maintain the desired total reactor pressure.

Evaporation Step

In the evaporation step (e.g., flash separation step), at least a portion of the reaction mixture is continuously withdrawn from the reactor 106 via line 120 and is introduced or fed to an evaporator and/or flasher 122. The reaction mixture is drawn off from the reactor 106 at a rate sufficient to maintain a constant level therein, and may be continuously withdrawn. The reaction medium may be separated in a flash separation step to obtain a vapor stream (flash overhead) 126 comprising acetic acid and liquid residuum stream 124 comprising a catalyst-containing solution. In some embodiments, the liquid residuum stream is recycled to the reactor 106 via line 124.

In some embodiments, a converter reactor (not shown) or a pipe reactor (not shown) can be employed in the flow path between the reactor and evaporator. A pipe reactor is described in U.S. Pat. No. 5,672,744 and is used to react the dissolved carbon monoxide in the reaction medium. Chinese Patent No. CN1043525C describes a converter reactor to allow the reaction to proceed to a greater extent prior to subsequent flashing.

The catalyst-containing solution collected in the lower portion of the flasher 122 may be predominantly acetic acid containing the rhodium and the iodide salt along with lesser quantities of methyl acetate, methyl iodide, lithium acetate and water and is recycled to the reactor. Prior to returning the liquid residuum to the reactor, a slip stream may pass through a corrosion metal removal bed, such as an ion exchange bed, to remove any entrained corrosion metals, such as nickel, iron, chromium, zinc, and molybdenum, as described in U.S. Pat. No. 5,731,252, which is incorporated herein by reference in its entirety. Also, the corrosion metal removal bed may be used to remove nitrogen compounds, such as amines, as described in U.S. Pat. No. 8,697,908, which is incorporated herein by reference in its entirety.

The evaporation step may include a thermostatic flash, an adiabatic flash, or a combination of these conditions. In some embodiments, the flasher 122 and/or reaction mixture may be heated during the evaporation step. In some embodiments, for example, the evaporation step may be carried out a temperature of about 100 to 250° C., e.g., from 110 to 200° C., from 120 to 180° C., from 125 to 170° C., or from 130 to 160° C. In some embodiments, for example, the pressure (gauge pressure) of the evaporator may be from 0.1 to 10 atm, e.g., from 0.3 to 10 atm, from 0.5 to 5 atm, from 0.8 to 3 atm, or from 1 to 2 atm.

Flasher 122 may be a vertical evaporator having a tori-spherical, ellipsoidal, or hemispherical head. To allow maintenance or access, flasher 122 may have one or more manways. The nozzle for reaction medium in line 120 may be in the upper portion of flasher 122, e.g., above the liquid level within the flasher 122. There may be one or more nozzles (not shown) that introduce the reaction medium tangentially to further disengage the vapor portion. In some embodiments, flasher 122 may have an upper portion with a larger cylinder diameter than the lower portion. flasher 122 should have large volume to allow the reaction medium that is fed thereto to be maintained in the flasher 122 to vaporize the desired carbonylation products into the vapor stream (flash overhead) 126, and prior to recycling the liquid residuum stream 124. In one embodiment, a residence time in the flasher 122 of about one minute or more is desirable, and in some embodiments, a residence time of at least about two minutes or more may be used.

In addition to acetic acid, vapor stream 126 also comprises methyl iodide, methyl acetate, water, PRC's and other iodide compounds. Dissolved gases exiting reactor 106 and entering flasher 122 comprise a portion of the carbon monoxide and may also contain gaseous by-products such as methane, hydrogen, and carbon dioxide. Such dissolved gases, unless consumed, exit flasher 122 as part of the vapor stream 126. In one embodiment, carbon monoxide in gaseous purge stream 108 may be fed to the base of flasher 122 to enhance rhodium stability.

In one embodiment, vapor stream 126 comprises acetic acid, methyl iodide, methyl acetate, water, acetaldehyde, and hydrogen iodide. In one embodiment, vapor stream 126 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor stream. In another embodiment, vapor stream 126 comprises acetic acid in an amount from 45 to 75 wt. %, methyl iodide in an amount from 24 to less than or equal to 36 wt. %, methyl acetate in an amount of less than or equal to 9 wt. %, and water in an amount of less than or equal to 15 wt. %, based on the total weight of the vapor stream. More preferably, vapor stream 126 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor stream 126 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde mass composition in the vapor stream may be in an amount from 0.005 to 1 wt. %, based on the total weight of the vapor stream, e.g., from 0.01 to 0.8 wt. %, or from 0.01 to 0.7 wt. %. In some embodiments, the acetaldehyde may be present in amounts less than or equal to 0.01 wt. %. Vapor stream 126 may comprise hydrogen iodide in an amount less than or equal to 1 wt. %, based on the total weight of the vapor stream, e.g., less than or equal to 0.5 wt. %, or less than or equal to 0.1 wt. %.

Vapor stream 126 may comprise methanol, and in particular low amounts of methanol. As noted above, methanol reacts with acetaldehyde to form the acetal 1,1,-dimethoxyethane. As also noted above, the inventors have found that, although the acetal-forming reaction is in equilibrium, it can be driven to completion with an excess (high mass composition) of methanol. Thus, in some embodiments, the mass composition of methanol in the vapor stream 126 may be controlled so as to control the mass composition of 1,1-dimethoxyethane in a liquid stream to be not more than 0.2 wt. %.

In some embodiments, an optional mist eliminator may be employed near the vapor outlet to coalesce liquid droplets. An optional scrubbing section (not shown) may further be employed in the vapor outlet of the flasher to prevent and/or reduce entrainment from metallic catalysts or other metallic components into the vapor stream 126. A wash liquid may be introduced into the optional scrubbing section. In another embodiment, an in-line separator may be used in the line for the vapor stream 126 to impart a swirling motion and allows any entrained liquid to coalesce. The liquid may be drained back to flasher 122 to reduce entrainment in vapor stream 126.

Liquid residuum stream 124 comprises acetic acid, the metal catalyst, corrosion metals, as well as other various compounds, including but not limited to formic acid, butyl acetate, and/or 1,1-dimethoxyethane. In one embodiment, liquid residuum stream comprises acetic acid in an amount from 60 to 90 wt. %, metal catalyst in an amount from 0.01 to 0.5 wt. %, corrosion metals (e.g., nickel, iron, chromium) in a total amount from 10 to 2500 wppm, lithium iodide in an amount from 5 to 20 wt. %, methyl iodide in an amount from 0.5 to 5 wt. %, methyl acetate in an amount from 0.1 to 5 wt. %, water in an amount from 0.1 to 8 wt. %, acetaldehyde in an amount of less than or equal to 1 wt. % (e.g., from 0.0001 to 1 wt. % acetaldehyde), and hydrogen iodide in an amount of less than or equal to 0.5 wt. % (e.g., from 0.0001 to 0.5 wt. % hydrogen iodide).

To handle the liquid residuum stream 124 in a manner that maintains flow rates, prevents equipment damage, and provides sufficient control, a vortex breaker (not shown) may be used near the liquid outlet of the flasher 122.

In some embodiments, the evaporation rate of the evaporation step (with or without heating) may be from 20 to 80% by mass, e.g., from 20 to 70%, from 25 to 75%, from 25 to 60%, from 25% to 50%, or from 30% to 40%.

First Distillation Step

In the first distillation step, at least a portion of the vapor stream 126 is fed (continuously fed) to a first distillation column (referred to as a light ends column or splitter column) 140. To allow for separation of the acetic acid in the vapor stream 126, the first distillation column 140 may comprise a plate column, a packed column or combination thereof. The vapor stream 126 is separated into a first overhead stream 142, a side stream 144, and a bottom stream 146. The first overhead stream 142 is withdrawn from the top of the first distillation column and/or an upper position of the first distillation column. The side stream 144 is a side-cut (liquid stream) which mainly contains acetic acid is taken from a position below the upper position of the overhead stream and above the inlet position of the vapor stream 126. The bottom stream 146 is withdrawn from a bottom portion of the first distillation column and/or a position lower than the inlet positions of the vapor stream 126. The proportion of the first overhead stream 142 may be about 20% to 60%, e.g., about 35% to 50%, of the vapor stream 126. The proportion of the side stream 144 may be about 30% to 80%, e.g., about 40% to 70%, of the vapor stream 126 and is generally larger than the first overhead stream 142. The proportion of the bottom stream 146 may be about 0% to 10%, e.g., from about 0% to 3%, of the vapor stream 126.

The first overhead stream preferably contains lower boiling impurities, such as water, methyl acetate, methyl iodide, and carbonyl impurities. The amount of water in the first overhead stream is generally greater than or equal to 5 wt. %. The carbonyl impurities present in the first overhead stream include acetaldehyde as well as various by-products derived from acetaldehyde, such as crotonaldehyde and 2-ethyl crotonaldehyde.

The side stream 144 preferably comprises a higher mass composition of acetic acid than the vapor stream 126. The amount of acetic acid may be greater than 80 wt. %, e.g., greater than 85 wt. % or greater than 90 wt. %. Nevertheless, the side stream 144 may comprise small amounts water and methyl iodide and/or methyl acetate. Water mass compositions in the side draw may vary depending on the reflux ratio, but are generally from 0.5 wt. % to 5 wt. %, e.g., from 0.6 to 3 wt. %, or from 0.7 to 2.8 wt. %. Methyl iodide, although preferably concentrating in the overhead, may also be present in lower amounts in the side draw 144 of not more than 6 wt. %, e.g., not more than 3 wt. % or not more than 1.7 wt. %. Similarly, methyl acetate mass compositions are lower in the side draw 144 than the overhead 142 and may be not more than 3 wt. %, e.g., not more than 1.5 wt. % or not more than 1.2 wt. %. To maintain high quality acetic acid, the side stream 144 contains substantially no amounts of 1,1-dimethoxyethane.

The acetic acid removed as the side stream 144 is preferably subjected to further purification, such as in the purifying step, the high-boiler removal step, iodine removal step, or combinations thereof. This further purification may remove water, higher boiling impurities, or other impurities from the stream, thereby producing an acetic acid product stream of high quality (purity). These steps are discussed in further detail below.

In one embodiment to sequester entrained catalyst, such as rhodium, from entering the further purification steps (distillation column) there may be a resin bed (not shown) downstream of first distillation column 140. The entrained catalyst may be in amounts of up to 100 ppb. This resin bed may operate to treat side stream 144 during steady state operations and may be taken off-line for reclamation. The resin bed downstream of first distillation column 140 benefits from a nickel-based or zirconium-based metallurgy due to the corrosive nature of the side stream 144. The resin bed may be a polymeric substrate which includes a polymer with nitrogen-containing heterocyclic repeat units, which includes, but is not limited to, vinyl pyrrolidone or vinyl pyridine resins. Such suitable resins are further described in U.S. Pat. No. 7,902,398, the entire contents and disclosures of which is hereby incorporated by reference.

The bottom stream 146 of the first distillation column typically contains at least water and acetic acid. The water in the bottom stream 146 may range from 0.5 wt. % to 5 wt. %, e.g., from 0.6 to 3 wt. %. The bottom stream 146 may also contain methanol, propionic acid, and other compounds. The bottom stream 146 may also contained an entrained metal catalyst (rhodium catalyst). The bottom stream 146 may be discharged, or a portion or the whole of the bottom stream may be recycled to the reaction step (reactor). The bottom stream 146 may be a liquid stream and may contain low levels of 1,1-dimethoxyethane.

The internal temperature of the first distillation column (light ends column, splitter column) 140 varies with the internal pressure. Operating pressure from 0.6 to 3 atm (gauge), e.g., from 0.7 to 1.5 atm, may be employed. For example, with an internal pressure of about 1 atm, the first distillation column may have a column top temperature (overhead temperature) of from 50 to 180° C., e.g., from 70 to 170° C., from 80 to 160° C., or from 90 to 150° C. In the embodiments that use a plate column, the theoretical number of plates may range from 5 to 80 plates, e.g., from 10 to 60 plates or from 15 to 50 plates.

The portion of the vapor stream 126 fed to and separated in the first distillation column is distilled at a sufficient residence time to enrich acetic acid in the side stream 124. Thus, in some embodiments, the residence time of the vapor stream 126 in the first distillation may be controlled so as to control the mass composition of 1,1-dimethoxyethane in a liquid stream to be not more than 0.2 wt. %. In particular, the residence time in the first distillation column may be controlled to not less than 30 seconds, e.g., not less than 1 minute, or not less than 5 minutes.

Phase Separation Step

As noted above, the first overhead stream 142 separated from the first distillation column 140 contains at least one reaction component, such as methyl iodide, methyl acetate, and water, and it is preferable to retain these reaction components within the process. The first overhead stream (light ends overhead) 142 is condensed by one or more condensers (heat exchangers) 148 into stream 150, which may be recycled to reactor 106 and/or refluxed to the first distillation column 140. An off-gas component may be vented from condensed first overhead stream 142 and subjected to subsequent treatment, as described below.

In some embodiments, first overhead stream 142 preferably may be condensed, e.g., in a condenser 148, and directed via line 150 to a receiver (overhead phase separation unit or decanter) 160. Conditions are desirably maintained such that the condensed first overhead stream 142 may separate in the receiver to form an upper phase (light phase, aqueous phase) 162 and a lower phase (heavy phase, organic phase) 164. Typically, the upper phase is enriched in water, and the lower phase is enriched in methyl iodide. The phase separation should maintain two separate phases, without forming a third phase or emulsion between the phases. An off-gas component 170 may be vented from decanter and subjected to subsequent treatment. In some embodiments, the average residence time of the condensed first overhead stream 142 in overhead decanter is greater than or equal to 1 minute, e.g., greater than or equal to 3 minutes, greater than or equal to 5 minutes, greater than or equal to 10 minutes, and/or the average residence time is less than or equal to 60 minutes, e.g., less than or equal to 45 minutes, or less than or equal to 30 minutes, or less than or equal to 25 minutes. In addition, overhead decanter may be arranged and constructed to maintain a low interface level to prevent an excess hold up of methyl iodide.

Upper phase 162 primarily includes water typically with methyl acetate, acetic acid, hydrogen iodide, acetaldehyde, dimethyl ether, methanol, and lesser amounts of methyl iodide. Methyl iodide concentrates in lower phase which further includes methyl acetate, acetaldehyde, dimethyl ether, hydrogen iodide, methanol, and lesser amounts of water and acetic acid. Other byproducts and impurities, such as but not limited to hydrogen iodide, formic acid, dimethyl ether, and crotonaldehyde, may be present in insignificant amounts. 1,1-dimethoxyethane mass composition in the upper and lower phases may be less than or equal to 2 wt. %, e.g., less than or equal to 1 wt. % or less than or equal to 0.5 wt. %. In some embodiments, the acetaldehyde mass composition in upper phase is larger, based on wt. %, than lower phase. For example, the upper phase may have the following composition shown in Table 1.

TABLE 1

| Upper Phase from Light Ends Overhead | | | |
|---|---|---|---|
| | (Wt. %) | (Wt. %) | (Wt. %) |
| Water | 40-80 | 50-75 | 60-75 |
| Methyl Acetate | 1-50 | 1-40 | 1-15 |
| Acetic Acid | 1-40 | 1-30 | 5-15 |
| PRC's (AcH) | <5 | <3 | <1 |
| Methyl Iodide | <10 | <5 | <3 |
| Methanol | <5 | <1 | 0.01-3.5 |
| Hydrogen Iodide | <1 | <0.5 | 0.001-0.5 |

A sufficient reflux stream may be obtained from the upper or lower phase. In some embodiments, a portion of upper phase 162 may be refluxed into first distillation column 140 via line 162*a*. The reflux ratio (amount of upper phase reflux/amount of the distillate of the upper phase) of upper phase to first distillation column 140 is from 0.5 to 20, e.g., from 0.5 to 15, from 1 to 15, or from 1.5 to 12. A portion of the upper phase 162 may be returned (recycled), e.g., to the reactor 106, via line 166.

Lower phase 164, which is primarily methyl iodide, is returned (recycled) to the reactor 106 via line 168. This allows the weight ratio of methyl iodide to water in the lower phase 164 to be greater than 1, e.g., greater than 3 or greater than 5. In some embodiments, a portion of lower phase may be refluxed alone or with the upper phase to the first distillation column 140. The specific gravity of lower phase may be from 1.3 to 2, e.g., from 1.5 to 1.8, from 1.5 to 1.75 or from 1.55 to 1.7. As described in U.S. Pat. No. 6,677,480, the measured specific gravity in lower phase may correlate to the methyl acetate mass composition in the reaction medium. As specific gravity decreases, the methyl acetate mass composition in the reaction medium increases. In some embodiments, receiver is arranged and constructed to maintain a low interface level to prevent an excess hold up of methyl iodide. For example, the lower phase may have the following composition shown in Table 2.

TABLE 2

| Lower Phase from Light Ends Overhead | | | |
|---|---|---|---|
| | (Wt. %) | (Wt. %) | (Wt. %) |
| Methyl Iodide | 60-98 | 60-95 | 75-93 |
| Methyl Acetate | 0.1-25 | 0.5-20 | 0.7-15 |
| Acetic Acid | 0.1-10 | 0.5-10 | 0.7-10 |
| Hydrogen Iodide | <1 | <0.5 | 0.001-0.5 |
| Water | <3 | 0.05-1 | 0.01-1 |
| PRC's (AcH) | <5 | <3 | 0.05-0.5 |
| Methanol | <5 | <2.5 | 0.01-2.5 |

The lower phase may comprise 1,1,-dimethoxyethane. The mass composition of 1,1-dimethoxyethane in the lower phase may be less than 0.2 wt. %, e.g., less than 0.15 wt. %, less than 0.1 wt. %, or less than 0.05 wt. %. The upper phase may also comprise 1,1-dimethoxyethane. The mass composition of 1,1-dimethoxyethane in the upper phase may be less than 0.2 wt. %, e.g., less than 0.15 wt. %, less than 0.1 wt. %, or less than 0.05 wt. %. Because the upper phase and/or the lower phase may comprise 1,1-dimethoxyethane, it is preferred that no stream comprising air or oxygen be allowed to contact the upper phase and/or the lower phase, so as to reduce the risk of oxidation.

The ratio, based on weight, of the flow rate of the upper phase withdrawn from the receiver relative to that of the lower phase withdrawn from the receiver may be, for example, about 0.1/1 to 10/1 (e.g., about 0.3/1 to 3/1) and preferably about 0.5/1 to 2/1 (e.g., about 0.7/1 to 1.5/1).

In a continuous process there may be variations in flow, which if left unregulated may cause disruptions and processing difficulties. To account for these variations the process may deploy a hold tank to buffer the streams between the first distillation column 30 and receiver, or after the receiver for either upper phase or lower phase. When used the hold tank is sized to account for up to 20% variations in flow entering and leaving the receiver.

Second Distillation Step; Acetaldehyde Separation Step

At least a portion of the upper phase and/or lower phase may be separated and directed to an acetaldehyde or PRC removal system via lines 162' or 164', respectively, to recover methyl iodide and methyl acetate during the acetaldehyde removal process. The upper phase and lower phase each contain carbonyl impurities (by-products), such as acetaldehyde, crotonaldehyde, and 2-ethyl crotonaldehyde, and the process may include the removal of these carbonyl impurities which deteriorate the quality (purity) of the acetic acid product.

FIG. 1 illustrates one embodiment of an acetaldehyde or PRC removal system 200 for processing the upper phase 162' and/or lower phase 164' (being a portion of the first overhead 142).

In one embodiment, either the upper or lower phase, or combinations thereof may be introduced via line 201 into a second distillation column 202, where acetaldehyde is removed in an second overhead 204 or the sidedraw 204', and 1,1-dimethoxyethane, including 1,1-dimethoxyethane formed within the column, falls down the column 202 and into the bottom stream (liquid) 206. The distillation may be conducted either as batch distillation or continuous distillation. To allow for separation, the second distillation column 202 may comprise a plate column, a packed column or combination thereof. In the embodiments that use a plate column, the theoretical number of plates thereof, may range from 1 to 100 plates, e.g., from 2 to 80 plates or from 5 to 75 plates.

The upper phase 162' and/or lower phase 164' is fed to a position between the first plate from the column top and the first plate above the column bottom. To prevent excess formation of 1,1-dimethoxyethane, the phases may be separated without the introduction of methanol into the distillation column 202. The feed to the distillation column 202 may contain lower amounts of methanol.

Any 1,1-dimethoxyethane within the distillation column 202, either fed to the distillation or formed within the column, descends into the bottom stream (liquid) 206. This liquid stream is withdrawn in the lower portion of distillation column 202, e.g., from the bottom of the column or near the bottom. The mass composition of 1,1-dimethoxyethane in the bottom stream (liquid) 206 may be less than 0.2 wt. %, e.g., from 0.001 to 0.2 wt. %, from 0.005 to 0.18 wt. %, or from 0.01 to 0.15 wt. %. In one embodiment, bottom stream (liquid) 206 has a mass ratio of methyl iodide to water that is greater than 1, e.g., greater than 3 or greater than 5.

Without being bound by theory, 1,1-dimethoxyethane is believed to form under conditions in the presence of acetaldehyde and methanol. Although methanol is fed to the reactor, methanol is rapidly converted and the mass composition of unreacted methanol in the reactor is too low for the formation of 1,1-dimethoxyethane. However, during the purification process there are zones in which the presence of acetaldehyde and methanol is sufficient to result in the formation of 1,1-dimethoxyethane.

In one embodiment, 1,1-dimethoxyethane has been found to form in sufficient quantities in a column that concentrates acetaldehyde into a stream. When concentrating acetaldehyde, the conditions in the column are sufficient to produce 1,1-dimethoxyethane which concentrates and collects in a liquid stream.

The total mass composition of permanganate reducing compounds (PRCs), of which acetaldehyde is a representative compound, in the feed composition (first mixture) to the distillation column 202 may vary from 0.05 to 50 wt. %, from 0.05 to 10 wt. %, from 0.1 to 5 wt. % or from 0.1 to 1 wt. %. Thus, a targeted amount of permanganate reducing compounds may be separated. As used herein, the terms "mass composition of permanganate reducing compounds" or "permanganate reducing compounds mass composition" may be the total mass composition of all the permanganate reducing compounds or may be the mass composition of each permanganate reducing compounds. The representative permanganate reducing compounds include acetaldehyde.

In addition to the permanganate reducing compounds (PRCs), the feed also comprises a mass composition of methyl iodide that is from 2.5 wt. % to 90 wt. %, e.g., from 10 wt. % to 85 wt. %, or from 20 to 70 wt. %, and a mass composition of water that is from 0.5 wt. % to 90 wt. %, e.g. from 1 wt. %, to 90 wt. %, or from 1.5 wt. %, to 85 wt. %. The feed composition may also comprise methyl acetate in an amount up to 30 wt. %, e.g. from 0.1 to 28 wt. %, or from 1 to 20 wt. %, acetic acid in an amount up to 25 wt. %, e.g., from 0.01 to 12 wt. %, or from 0.5 to 7.5 wt. %, dimethyl ether in an amount up to 1 wt. %, e.g., from 0.001 to 1 wt. %, or from 0.004 to 0.8 wt. %, and methanol in an amount of less than or equal to 2 wt. %, e.g., less than or equal to 1.8 wt. %, less than or equal to 1.5 wt. %, less than or equal to 1.1 wt. %, less than or equal to 1.0 wt. %, or less than or equal to 0.5 wt. %.

The feed composition may be a homogeneous liquid or a mixture of the lower and upper phases.

Second distillation column 202 operates to separate a second mixture, which may be withdrawn as an overhead stream 204 or sidedraw 204', and a bottom stream (liquid) 206. In some embodiments, the second mixture 204/204' comprises overhead stream (or a portion thereof) and/or sidedraw (or a portion thereof). The extraction in second distillation column 202 yields a second mixture that contains significantly more acetaldehyde than the feed. Thereby the ratio, on a weight basis, of acetaldehyde to methyl iodide in the second mixture 204/204' is greater than the acetaldehyde to methyl iodide ratio in the feed. Second mixture contains acetaldehyde, which is the principal PRC, which has been distilled or processed in second distillation column 202 and may be subsequently processed to remove acetaldehyde from the process or reduce the mass composition of acetaldehyde, as described further in detail. Second mixture may be withdrawn higher than, nearer to the top of the second distillation column 202, than that of the first location. To provide rectification, in one embodiment, there may be at least one or more actual plates between the first location and the withdrawn location of the second mixture 204/204'.

In one embodiment, acetaldehyde may be separated from methyl iodide in an efficient process that reduces the loss of methyl iodide, and may function or operate even when first mixture is made to comprise methyl acetate, methanol, acetic acid, or combinations thereof. In particular, acetaldehyde is separated from the first mixture to reduce the mass composition of acetaldehyde in the bottom stream (liquid) 206. The bottom stream 206, owing to the relative amounts of methyl iodide and methyl acetate, may be returned as a recycle (directly or indirectly) to the reactor 102. Indirect recycle refers to a process whereby the stream passes through another vessel prior to returning to the reactor 102. Direct recycling may include combine the recycle stream with one or more other recycle streams.

Even though acetaldehyde mass composition in bottom stream (liquid) 206 is reduced or suppressed, it is also useful to control reaction byproducts of acetaldehyde, which may be converted to acetaldehyde upon recycling. In particular, one byproduct of acetaldehyde that tends to form in the extractive step of the second distillation column 202 may be an acetal, which includes but is not limited to 1,1-dimethoxyethane. Through various secondary or side reactions with methanol, acetaldehyde may be converted to 1,1-dimethoxyethane. Owing to the relatively higher boiling point of acetals as compared to the aldehyde, the acetals fall into the bottom stream (liquid) 206, which is subsequently recycled. For example, 1,1-dimethoxyethane has a boiling point of 64° C. The formation of acetal reduces the efficiency of second distillation column, because instead of effectively removing acetaldehyde, the second distillation column 202 allows the acetal to build up in the lower portion and is returned to the reactor. Through a reversible reaction may yield acetaldehyde from the recycled acetal and decreases the effectiveness of second distillation column 202. There are a number of factors that can lead to acetal increases, which includes when excessive methanol is introduced to the second distillation column 202, either in the first mixture or separately. Temperature and reflux ratio of the second distillation column 202 may also influence the acetal mass compositions.

In one embodiment, bottom stream (liquid) 206 comprises 1,1-dimethoxyethane in a mass composition that is not more than 0.2 wt. %, e.g., not more than 0.18 wt. %, not more than 0.15 wt. % or not more than 0.1 wt. %. Maintaining such low levels is useful to increase the robustness of the process against air (oxygen) intrusion that may cause formation of peroxides. As discussed herein, the formation of peroxides gives rise to a number of issues.

Feed composition to the second distillation column 202 may comprise a portion of the upper phase 162' or lower phase 164'. This allows the feed to be introduced to second distillation column 202 at a location above the first plate from the bottom.

Figure 2:
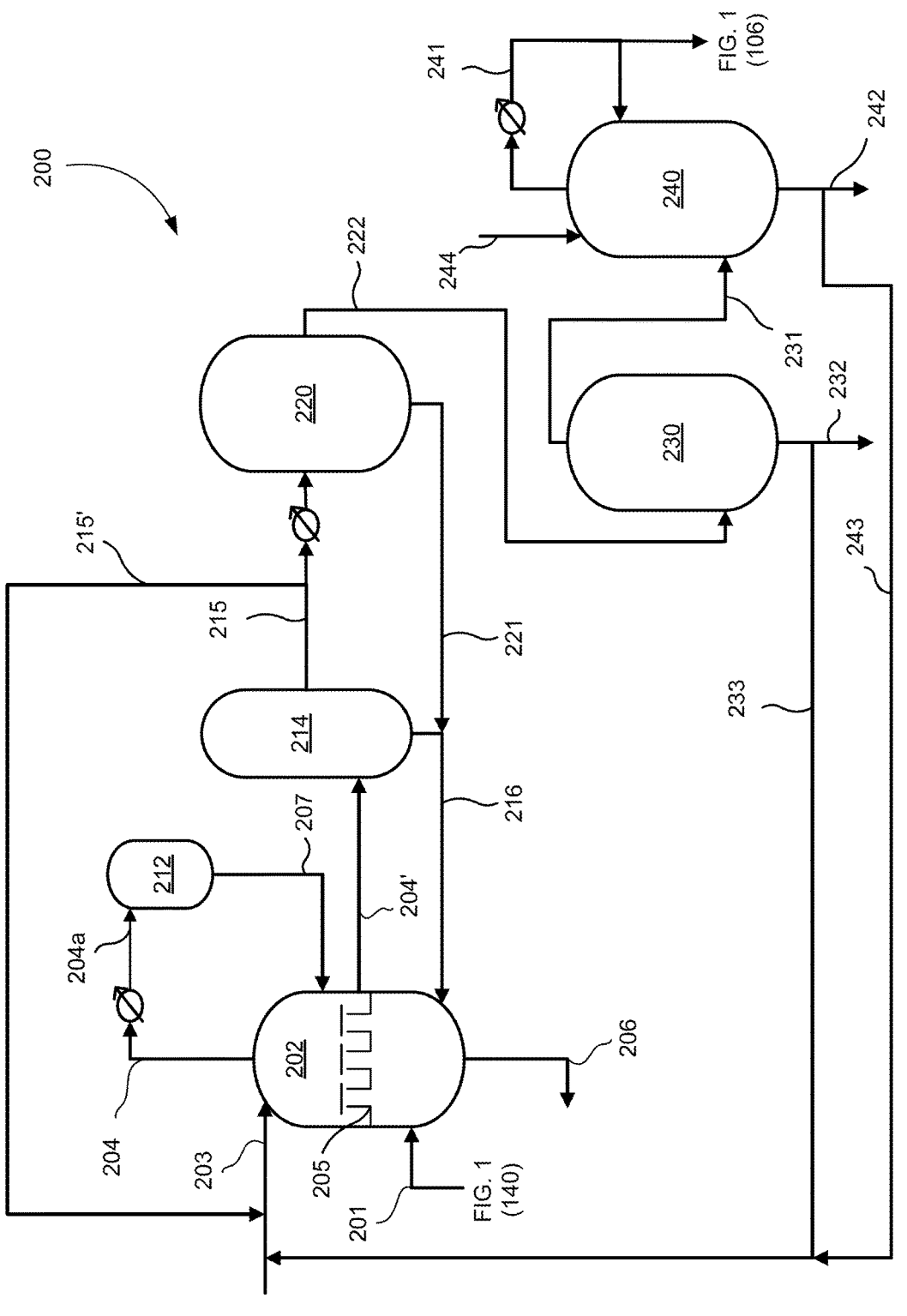
FIG. 2 illustrates a schematic of an acetaldehyde or PRC removal system in accordance with embodiments of the present disclosure.
Figure 3:
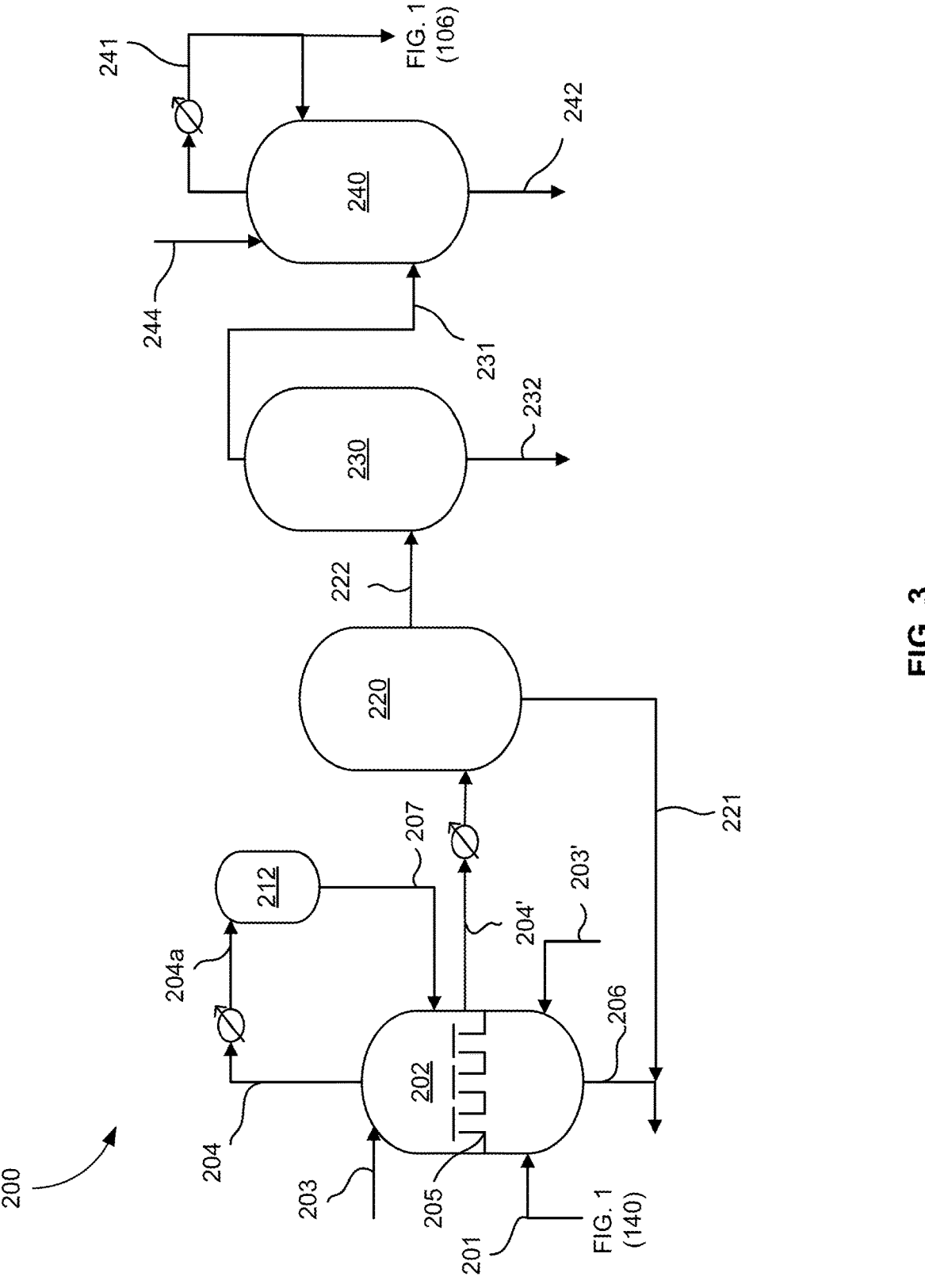
FIG. 3 illustrates a schematic of an acetaldehyde of PRC removal system in accordance with embodiments of the present disclosure.

In addition, second distillation column 202 may be fed with an extractant having a suitable composition for extracting acetaldehyde from the mixture, which is shown as the extractant 203 in FIGS. 1-3. The extractant may be suitable composition for extracting acetaldehyde from the first mixture. For ease of processing, the extractant may also be separable from methyl iodide using a low energy technique including liquid-liquid separation and/or membrane separation. The extractant may comprise extracting water, a mixed solvent or a water-soluble organic solvent (glycol, glycerin, acetones, ethers, and/or esters). Introducing water is advantageous to maintain the extracting mixture in a liquid-liquid separation state and thus, the extractant is made to comprise not less than 80 wt. % water, e.g., not less than 90 wt. % water, or not less than 95 wt. % water. In one embodiment, to prevent excess formation, the extractant practically does not comprise methanol, or other mono-alcohols. Thus, additional methanol is not fed into the second distillation column 202. Despite water or a water-containing extractant being preferred extracting mixtures, in some embodiments, second distillation column 202 may distill the upper and/or lower phases without additional water.

In one embodiment, the water supply may be a fresh source of water external to the process. In another embodiment, the water supply for the extractant may be an internal stream containing water that is redirected to the top of the second distillation column 202. Any suitable internal stream may be used, as described further herein. In one embodiment, internal streams that are deficient in methanol are preferred to be used as the extractant, including internal streams having a methanol mass composition of less than or equal to 0.1 wt. %. When the internal streams contain higher amounts of methanol these internal streams may be treated to reduce the methanol mass compositions in a suitable manner. Any acetaldehyde or other PRC contained in these internal streams may be recovered in the second mixture 204/204'.

As shown in FIG. 2, second distillation column 202 separates the components introduced thereto through extractive distillation. In one embodiment, the feed line may be extracted with an extractant 203 that is introduced in an upper zone of the second distillation column 204 is above the first location. In one embodiment, extractant 203 may be introduced in top of the second distillation column 202, separate from the first location. Thus, in embodiments where the extractant 203 is made to comprise a portion of the upper phase 162', the upper phase 162' is fed above and separately from the feed. The mass composition of PRC is higher in the upper zone and introducing the extractant 203 to this zone yields an extractant mixture, which is withdrawn as a second mixture (either an overhead 204 or sidedraw 204') that is enriched in acetaldehyde, as well as other PRCs. In one embodiment, the second mixture 204/204' comprises less than or equal to 2 wt. % methanol, e.g., less than or equal to 1 wt. % methanol or less than or equal to 0.5 wt. % methanol. A relatively lower amount of extractant may be used when the PRCs, including acetaldehyde, are extracted into the second mixture (overhead 204 or sidedraw 204') as opposed to the lower stream. For example, the flow rate ratio (on a weight basis) of the extractant 203 relative to feed composition may range from 0.0001/100 to 100/100, e.g. 0.001/100 to 50/100, 0.0001/100 to 20/100, 0.001/100 to 10/100, 0.01/100 to 8/100, or 0.1/100 to 5/100.

In a case where the feed composition fed to second distillation column 202 contains the lower phase 164' after being liquid-liquid separated, the first mixture may have the composition shown in Table 2 above. Although not necessarily preferred, in a case where feed composition contains the upper phase 162' from the liquid-liquid separation, this feed may have the composition shown in Table 1 above.

In using an extractive distillation in the second distillation step, PRC's and/or the methyl iodides may be processed in an efficient manner that reduces the energy requirements.

By using an extractive distillation, the number of stages for the second distillation column 202 may be reduced. In one embodiment, second distillation column has less than or equal to 100 stages, e.g., less than or equal to 80 stages or less than or equal to 45 stages. To illustrate the feed locations and the location of the withdrawn second mixture, the following example is provided using 50 stages, where bottom 52 is the $0^{th}$ plate, and the overhead 51 is the $50^{th}$ plate. These illustrative examples can be applied to a distillation column having a different amount of stages or plates. The first location, where the feed line 201 is introduced may be selected in the range from the $1^{st}$ plate to the $35^{th}$ plate, e.g., from the $3^{rd}$ plate to the $25^{th}$ plate or the $5^{th}$ plate to the $20^{th}$ plate. The second location for withdrawing the sidedraw, may be selected in the range from the $20^{th}$ to $49^{th}$ plate, e.g., from the $25^{th}$ to $48^{th}$ plate or from the $35^{th}$ to $48^{th}$ plate, provided that the second location is withdrawn from a plate, such as a collector tray, above the first location. In one embodiment, there may be at least 1 plate separating the second location and first location, e.g., at least 5 plates of separation. Although the extractant 203 may be added at the top, e.g., $50^{th}$ plate, in some embodiments, the extractant may be added a location selected in the range from the $45^{th}$ to $50^{th}$, e.g., from the $45^{th}$ to $49^{th}$ plate.

The extraction efficiency may increase by countercurrently adding the extractant 203 to an upper zone of the second distillation column 202. Further, the extractant 203 may be added by spraying or sprinkling or any other suitable method, including adding in a droplet form. In one embodiment, the extractant 203 may have a temperature from 0° C. to 60° C., e.g., 10° C. to 50° C., and 20° C. to 40° C. In other embodiment, the process may involve pre-heating or warming of the extractant to a temperature from 30° C. to 150° C., e.g., 50° C. to 110° C. or from 60° C. to 110° C.

The second distillation column 202 of FIG. 2 includes a collector tray (plate) 205, which may be referred to as a hat tray or chimney tray, to allow the good vapor distribution to the upper zone from the feed line 201 and the holding of the whole amount of the extraction mixture to be taken off as sidedraw 204'. Any suitable design for the collector tray 205 may be used with the embodiments described herein. The collector tray 205 is practically located where the sidedraw 204' is taken and thus the extractant 203 is be added above the collector tray 205. This allows the falling liquid from the upper portion of the second distillation column 202 to be received on collector tray 205. Although not shown in FIG. 2, in a case where the collector tray 205 is disposed at a position lower than the feed location of the mixed composition, the collector tray 205 is positioned above the bottom stream 206.

In one embodiment, the second distillation column 202 is provided with at least one collector tray 205, e.g., two or more collector trays 205. For a distillation column 202 having a plurality of collector trays, the extractant 203 may be added above uppermost collector tray.

In one embodiment, the second distillation column 202 is provided with a collector tray 205, the extractant (or extracting water) 203 is added to the upper zone above the collector tray 205. The upper zone is formed in a space between the first location and the top of the distillation column 202. Acetaldehyde has a relatively low boiling point as a PRC, and methyl iodide has a relatively low boiling point as a $C_1$-$C_{12}$ alkyl iodide, which forms in the upper zone and a second mixture is withdrawn from the upper zone as stream 204 and/or 204'. In one embodiment, the collector tray 205 may be disposed at an upper position of the second distillation column 202. The PRCs are extracted efficiently by withdrawing the sidedraw 204' from the upper zone, and thus the position of the collector tray 205 is practically upper than the first location for the feed line 201 (mixed composition). The collector tray 205 is not limited to a particular position, and may be disposed at the same height level as the height level of the first location or may be disposed in a lower zone below the first location.

The height level of the collector tray 205 in the second distillation column 202 is upper than the first location of the feed line 201. In cases when a collector tray 205 is used, the collector tray may replace a plate in the distillation column. According to the number of plates of the second distillation column, the height level of the collector tray 205 is in between the uppermost plate of the column (the 1st plate from the top of the column) and a plate at least one plate upper than the feed line 201 or is positioned at or near the top of the second distillation column. In a case where the total number of plates of the distillation column is 40, the height level of the collector tray 205 may be selected from the range corresponding to the $1^{st}$ to the $35^{th}$ plate from the top of the distillation column, e.g., from $2^{nd}$ to $30^{th}$ plate, or from $2^{nd}$ to $15^{th}$ plate. These illustrative examples can be applied to a distillation column having a different amount of stages or plates.

The operating conditions for the second distillation column 202 are configured to maintain the extractive environment for recovering the second mixture 204/204'. As understood the internal temperature of the second distillation column 202 is related to the column top pressure (absolute). This pressure is generally controlled or maintained within pressure from 100 kPa to 500 kPa, e.g., from 100 kPa to 250 kPa, or from 100 kPa 100 to 200 kPa. At atmospheric pressure (approximately 101 kPa), the second distillation columns operates with a top temperature from 15° C. to 120° C., e.g., from 15° C. to 100° C. or from 15° C. to 80° C., and bottom temperature from 35° C. to 165° C., e.g., 202° C. to 150° C., or 202° C. to 115° C. In one embodiment, the bottom temperature is maintained above a temperature that maintains acetaldehyde in a gaseous state below the collector tray 205 to drive the acetaldehyde towards the upper zone for extracting into the second mixture 204/204'.

Depending on the mixed composition in feed line 201, acetaldehyde may be effectively extracted into the second mixture 204/204', notwithstanding that presence of methyl acetate and/or acetic acid, which tend to have an affinity with both PRCs (including acetaldehyde) and $C_1$-$C_{12}$ alkyl iodides (including methyl iodide). In one embodiment, the mass composition of acetaldehyde in the second mixture (including the overhead 204 and/or sidedraw 204') is from 5 to 1000 times more than the amount in the feed composition on a weight basis, e.g., from 10 to 500 times or from 20 to 300 times.

In one embodiment, the second mixture 204/204' is taking from the sidedraw 204' and the overhead 204 is condensed and refluxed at the top of the second distillation column 202. The reflux ratio, which is the amount of the overhead refluxed/the amount of overhead distilled, to the second distillation column at a reflux ratio from 0.2 to 15, e.g., from 0.5 to 15, from 1 to 15, or from 2 to 10. In some embodiments, there may be a distillate that is removed from the top of the second distillation column 202, but generally the condensed portion of the overhead 204 is refluxed. The overhead 204 exits second distillation column 202 with a temperature from 15° C. to 120° C. A condenser (or plurality of condensers as needed) may condense the overhead 204 to a temperature lower than the boiling point of methyl iodide. The condensed liquid 204a is accumulated in an overhead receiver 212 and refluxed via line 207. To maintain extractive conditions, line 207 may enter second distillation column 202 between the location of the extractant 203 and withdrawing location of sidedraw 204' (e.g., above collector tray 205). This reflux can be used to prevent excess amounts of extractant and namely water, from being presence in the overhead 204.

In a lower portion of second distillation column 202 a miscible solvent may be directly or indirectly fed. This solvent is miscible with a process stream containing methyl iodide. The miscible solvent may be at least one component selected from the group consisting of water, acetic acid, methyl iodide, and methanol. When added, the miscible solvent may be not more than 30 wt. % relative to the amount of the sidedraw 204' withdrawn from collector plate 55, e.g., not more than 15 wt. %, or not more than 10 wt. %.

The composition of overhead 204 in general has a total amount of PRC and $C_1$-$C_{12}$ alkyl iodides that greater than the total mass composition of the remaining organic components. In one embodiment, the composition of the overhead 204 may have a total PRC mass composition from 1 to 75 wt. %, e.g., from 5 to 65 wt. % or from 10 to 50 wt. %, and $C_1$-$C_{12}$ alkyl iodides mass composition from 1 to 85 wt. %, e.g., from 10 to 80 wt. %, or from 20 to 60 wt. %. The remaining organic components may comprise methyl acetate, acetic acid, methanol, and dimethyl ether, and are in various amounts which can include amounts of less than or equal to 10 wt. %, e.g., less than or equal to 5 wt. %. The water mass composition in the overhead 204 may be less than the water in the feed composition in feed line 201. The overhead 204 may have a water mass composition that is not more than 20 wt. %, e.g., not more than 15 wt. %, not more than 10 wt. % or not more than 5 wt. %. The overhead 204 may have a methyl acetate mass composition of up to 10 wt. %, e.g., up to 5 wt. %, or up to 1 wt. %. The overhead 204 may have an acetic acid mass composition of up to 10 wt. %, e.g., up to 5 wt. %, or up to 1 wt. %. Generally it is desired to have the lowest possible acetic acid mass composition by reducing the acetic acid in the feed line 201. Likewise the mass compositions of dimethyl ether and methanol in the overhead may also be maintained at low levels. The mass composition of dimethyl ether in the overhead may be not more than 1.8 wt. %, e.g., not more than 1.5 wt. %, or not more than 1 wt. %, and the mass composition of methanol in the overhead may be not more than 0.55 wt. %, e.g., not more than 0.35 wt. % or not more than 0.25 wt. %.

In some embodiments, the second mixture may be the overhead 204 or may comprise a portion of the overhead 204. In some embodiments, the overhead 204 is condensed and a distillate portion is used as the second mixture for removing PRCs. In the embodiment shown in FIG. 2, the composition of overhead 204 may be phase separable in overhead receiver 212 into an aqueous phase 208 and an organic phase 207. The organic phase 207 may be enriched in methyl iodide and deficient in water, while the aqueous phase 208 may contain useful amounts of PRCs and water.

Sidedraw 204' (second mixture) is withdrawn as a liquid stream from distillation column 202. As a result of the extractive nature of the distillation column 202, sidedraw 204' may have a ratio, based on weight, of PRC to alkyl iodides (e.g., ratio of acetaldehyde to methyl iodide), that is greater than the ratio of PRC to alkyl iodides in the feed composition. This further concentrates PRC for removal. The process according to the present invention concentrates the PRC without building up large quantities of acetals. In one embodiment, the composition of the sidedraw 204' may have a PRC mass composition from 0.1 to 90 wt. %, e.g., from 0.2 to 65 wt. % or from 0.5 to 50 wt. %, $C_1$-$C_{12}$ alkyl iodides mass composition from 0.5 to 95 wt. %, e.g., from 1 to 95 wt. %, from 5 to 90 wt. %, or from 10 to 60 wt. %, methyl acetate mass composition from 0.1 to 25 wt. %, e.g., from 0.5 to 20 wt. %, or from 0.5 to 10 wt. %, acetic acid mass composition from 0 to 10 wt. %, e.g., from 0.01 to 5 wt. %, or from 0.05 to 1 wt. %, water mass composition from 0.1 to 20 wt. %, e.g., from 0.5 to 15 wt. %, or from 0.5 to 8 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %.

As shown in FIG. 2, the condensed overhead 204a is collected in vessel 214. Vessel 214 may be a buffer tank or may be a liquid-liquid separation vessel capable of receiving the second mixture and separating the condensed overhead 204a into phases. In some embodiments, vessel 214 separates the liquid-liquid separable condensed overhead 204a into an aqueous phase 215 and an organic phase 216. PRCs, including acetaldehyde, distributes more favorably into the aqueous phase 215 than organic phase 216. In addition, the extractant is more favorably separated into aqueous phase 215, and the extractant may be recovered through subsequent processing of the aqueous phase, although it is not necessary to recover the extractant. The organic phase may be returned to second distillation column 202 or combined with the bottom stream 206 and is returned to the reactor 106. In addition, it is desirable to have reduced amounts of methyl iodide in the aqueous phase 215 so that the acetaldehyde may be discharged without further processing.

In one embodiment, the vessel 214 separates the second mixture 204' into an aqueous phase 215 and organic phase 216. The mass flow ratio of the aqueous phase 215 and the organic phase 216 may be from 1:1000 to 1:1 (aqueous phase to organic phase), e.g., from 1:900 to 1:10 or from 1:650 to 1:100. On balance, the aqueous phase may be the smaller stream, based on the mass flow, than the organic phase. The organic phase 216 is deficient in the extractant and may be returned to the second distillation column 202.

The aqueous phase 215 has higher PRCs (acetaldehyde) mass composition than the organic phase 216, and the aqueous phase 215 may have a higher mass composition of PRCs than $C_1$-$C_{12}$ alkyl iodides (methyl iodide). Using acetaldehyde and methyl iodide as representatives, the aqueous phase 215 may have a ratio of former to latter, on a weight, from 2:1 to 60:1, e.g., from 3:1 to 45:1, from 3:1 to 30:1, or from 4:1 to 20:1. The composition of aqueous phase 215 comprises a PRC (acetaldehyde) mass composition from 1 to 50 wt. %, e.g., from 5 to 45 wt. % or from 10 to 35 wt. %, water mass composition from 40 to 95 wt. %, e.g., from 50 to 90 wt. %, or from 60 to 75 wt. %, $C_1$-$C_{12}$ alkyl iodides (methyl iodide) mass composition from 0.01 to 15 wt. %, e.g., from 0.1 to 10 wt. %, or from 0.5 to 6 wt. %, methyl acetate mass composition from 0.1 to 25 wt. %, e.g., from 0.5 to 20 wt. %, or from 0.5 to 10 wt. %, acetic acid mass composition from 0 to 5 wt. %, e.g., from 0.01 to 2.5 wt. %, or from 0.05 to 1 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %.

The organic phase 216 may be returned to second distillation column 202 below the collector tray 205. In one embodiment, the composition of organic phase 216 comprises a $C_1$-$C_{12}$ alkyl iodides (methyl iodide) mass composition from 0.1 to 90 wt. %, e.g., from 5 to 85 wt. %, or from 10 to 80 wt. %, methyl acetate mass composition from 0.1 to 30 wt. %, e.g., from 0.5 to 20 wt. %, or from 0.5 to 10 wt. %, PRC (acetaldehyde) mass composition from 0.01 to 15 wt. %, e.g., from 0.5 to 10 wt. % or from 0.5 to 5 wt. %, acetic acid mass composition from 0 to 5 wt. %, e.g., from 0.01 to 2.5 wt. %, or from 0.05 to 1 wt. %, water mass composition from 0.01 to 5 wt. %, e.g., from 0.05 to 4 wt. %, or from 0.5 to 3.5 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %.

To operate effectively, in one embodiment the lower stream 207 contains a significant portion of the methyl iodide from feed composition, in particular when feed composition is made to comprise a portion of the lower stream 164'. The lower stream 207 of distillation column 202 contains useful methyl iodide that is returned to the reactor 106. To achieve production, the distillation column removes 60 to 99.9% of the methyl iodide in the feed composition into the lower stream 207, e.g., from 75 to 99.5% or from 80 to 99.1%. Successful removal of methyl iodide provides a lower stream 207 having a mass composition of $C_1$-$C_{12}$ alkyl iodides (methyl iodide) from 10 to 90 wt. %, e.g., from 15 to 85 wt. %, or from 20 to 80 wt. %. However, in doing so, this increases the 1,1-dimethoxyethane return to the reactor. To overcome these shortcomings and to efficient use the lower stream 207, the water mass compositions are maintained at sufficient levels to transform or convert the 1,1-dimethoxyethane.

The bottom stream 206 also comprises a deficient amount of water, which is unable to transform the 1,1-dimethoxyethane to any great extent. This allows the mass ratio of methyl iodide to water to be greater than 1, e.g., greater than 3 or greater than 5. In one embodiment, the water mass composition of the bottom stream 206 is less than 1.5 wt. %, e.g., less than 1.1 wt. %, less than 1.0 wt. %, less than 0.7 wt. %, or less than 0.5 wt. %. The acetaldehyde content is expected to be very small in the bottom stream 206 and may be less than 0.05 wt. %, e.g., less than 0.04 wt. %, less than 0.02 wt. %, or less than 0.005 wt. %. Methanol mass compositions are likewise relatively small in the liquid stream and generally are less than 1 wt. %, e.g., less than 0.8 wt. %, less than 0.5 wt. %, or less than 0.1 wt. %. Methyl acetate and acetic acid may accumulated in the liquid stream 42, and the respective mass composition for methyl acetate is from 5 to 60 wt. %, e.g., 10 to 50 wt. %, or 10 to 35 wt. %, and acetic acid is from 1 to 20 wt. %, e.g., from 1.5 to 15 wt. %, or from 2 to 10 wt. %.

The lower stream 207 may be withdrawn at a temperature from 30° C. to 1214° C., e.g., 35° to 120° C., or 202° C. to 100° C.

Supplementary Acetaldehyde Removal

Although acetaldehyde, including other PRCs, are removed in the second mixture 204/204' from the second distillation column 202, it may be desirable to remove or reduce acetaldehyde through supplementary processing and recover either useful organic components and/or extractant. There are several available methods for achieving such supplementary removal of acetaldehyde. For the purposes of present invention, these supplementary removal processes if used at all, can vary depending on the requirements on the processing facility. One aspect of supplemental acetaldehyde removal is that the process should not increase the 1,1-dimethoxyethane mass composition in the lower stream 207.

In one embodiment, acetaldehyde may be removed or reduced by purging the second mixture 204/204' from the process. This may be done with the second mixture 204/204' that contains very low amounts of methyl iodide, in particular amounts that are less than 1 wt. %, e.g., less than 0.5 wt. %. When the second mixture 204/204' contains higher amounts of methyl iodide it may be desirable to avoid purging of the second mixture 204/204' by employing a supplemental acetaldehyde removal process.

In another embodiment, there may be a second extraction step of the second mixture 204/204' in an extractor having no stages or distillation column having stages. For this supplemental acetaldehyde removal process, the second extraction uses a secondary extractant (additional water) and may yield an extractant containing the acetaldehyde and a raffinate containing the methyl iodide. This allows the raffinate to be recovered and the extractant to be further disposed of or purged. Under this arrangement, the second extraction may be positioned as a consecutive stage with the second distillation column 202. There may be a condenser/chiller between the extraction stages, i.e. the second distillation column 202 and extractor. The temperature of the second mixture 204/204' using the condenser/chiller may be from 10° C. to 80° C., e.g., from 12° C. to 65° C. or from 13° C. to 45° C.

In one embodiment, the acetaldehyde separation step comprises separating the second mixture 204/204' in one or more extractors and/or one or more additional distillation columns.

FIG. 2 illustrates another embodiment of an acetaldehyde or PRC removal system 200. As shown in FIG. 2, the feed composition is represented as the overhead 201, but it should be understood that the feed composition may comprise a portion of the overhead 201, including the liquid-liquid separated upper and lower streams described above. After the feed composition is distilled and/or extracted in distillation column 202, the second mixture is withdrawn as sidestream 204' from second distillation column 202 and introduced to vessel 214. The overhead 204 is condensed and the condensed portion 204a is refluxed via line 207. Water is used an extractant 203 and introduced to the top of the second distillation column 202. The lower stream 206 is removed from the bottom of second distillation column 202 and is recycled to a vessel containing at least 1.5 wt. % or more of water to transform 1,1-dimethoxyethane contained therein. The organic phase 216 from vessel 214 is recycled to a lower portion of second distillation column 202. The organic phase 216 being rich in methyl iodide as compared to the second mixture, may be recycled to a position lower than the position for withdrawing the sidedraw 204', e.g., lower than the collector tray 205. The organic phase 216 from vessel 214 may also be recycled to the reactor (not shown).

The portion of sidedraw 204' that contains relatively more acetaldehyde in the aqueous phase 215. Aqueous phase 215, owing to its water content, may present as a suitable extracting mixture for second distillation column 202 and a portion thereof in line 215' may be recycle as the extractant 203. This recycle portion in line 215' may comprise the whole extractant 203 or may be combined with additional sources of water to comprise a portion of the extractant 203. In one embodiment, aqueous phase 215 is not used as an extracting mixture and line 215' may be have a closable valve or line 215' may be removed from the process.

Similar to the relatively high temperature of the sidedraw 204' (second mixture), the aqueous phase 215 from vessel 214 may be cooled by passing through a condenser (cooler) prior to be collected in decanter 220. Cooling water may be used as the coolant. The temperature of the aqueous phase 215 may be from −5° C. to 60° C., e.g., from 0° C. to 30° C. or from 3° C. to 20° C.

In the decanter 220, there may be a residual amount of methyl iodide that is separable by a liquid-liquid separation into a residual stream 221. The residual stream 221 contains more methyl iodide than aqueous phase 215. The residual stream 221 (a heavy phase rich in methyl iodide or a lower phase) formed in the decanter 220 is recycled to the second distillation column 202 by either being combined with the organic phase 216 of vessel 214 or being added to the second distillation column 202 below the collector plate 205. Although residual stream 221 may bypass the second distillation column 202 and be returned to reactor 106 with lower stream 206, it is preferred to first reduce impurities in residual stream 221 prior to returning to reactor 106. To prevent phase issues, it is not advisable to introduce residual stream 221 back into vessel 214.

Decanter 220 also yields a liquid stream 222. The liquid stream 222 contains the targeted acetaldehyde to be removed. The mass flow ratio of the liquid stream 222 and the residual stream 221 may be from 1:500 to 1:0.5 (liquid to residual), e.g., from 1:400 to 1:1 or from 1:375 to 1:10. Despite the smaller relative stream, the liquid stream 222 contains an useful amount of acetaldehyde. The acetaldehyde mass composition in liquid stream 222 based on amount may be more than 2× (two times) the amount in residual stream 221, e.g., more than 3× or more than 4×.

Although the liquid stream 222 may be disposed of to reduce the acetaldehyde mass composition, there may be processes which seek to further retain methyl iodide and/or the extractant (water) used for the extracting mixture. Thus, the liquid stream 222, or a portion thereof, may be further subjected to separation using a third distillation column 230. In such a distillation, third distillation column 230 yields an overhead stream 231 containing acetaldehyde in an amount from 1 to 99 wt. % and methyl iodide in an amount from 0.1 to 30 wt. %, and a bottoms stream 232 containing the extractant as the main component in an amount of not less than 10 wt. %, and methyl iodide in an amount of not more than 1 wt. % (provided that, each stream, including impurities, has a total amount of 100% by weight). A portion of the bottoms stream 232 may be used as the extractant via line 233 and returned to second distillation column 202. In other embodiment, bottoms stream 232 may be removed or discharged from the process.

The third distillation column 230 may have a column top pressure (absolute) from 100 to 500 kPa, e.g., 115 to 375 kPa and 125 to 250 kPa. To effectively separate the overhead, the third distillation column 230 at atmospheric pressure has a temperature at the column top from 10 to 90° C., e.g., from 15 to 80° C. or 20 to 60° C., and/or a column bottom temperature from 70 to 170° C., e.g., from 80 to 160° C. or from 90 to 150° C. The number of stages (plates) in the third distillation column 230 may be a sufficient number for separation, for example, from 1 to 50 plates, e.g., from 2 to 45 plates or from 3 to 30 plates. The reflux ratio (reflux: distillate) of the third distillation column 230 is from 1:20 to 20:1, e.g., from 1:15 to 15:1, or from 5:1 to 10:1.

The overhead stream 231 or a distillate thereof contains more acetaldehyde and has a lower methyl iodide mass composition than second mixture. In one embodiment, the composition of overhead stream 231 comprises a PRC (acetaldehyde) mass composition from 45 to 99 wt. %, e.g., from 50 to 99 wt. % or from 60 to 98 wt. %, $C_1$-$C_{12}$ alkyl iodides (methyl iodide) mass composition from 0.1 to 30 wt. %, e.g., from 0.5 to 25 wt. %, or from 1 to 20 wt. %, methyl acetate mass composition from 0.1 to 25 wt. %, e.g., from 0.5 to 20 wt. %, or from 0.5 to 12 wt. %, acetic acid mass composition from 0 to 5 wt. %, e.g., from 0 to 1.5 wt. %, or from 0 to 1 wt. %, water mass composition from 0 to 5 wt. %, e.g., from 0 to 2.5 wt. %, or from 0.01 to 2 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. In one embodiment, the overhead stream 231 has a ratio (based on weight) of methyl iodide relative to acetic acid is that higher than this ratio in feed to the third distillation column 230. In addition or separately, the overhead stream 231 may have a ratio (based on weight) of methyl iodide relative to methyl acetate is that higher than this ratio in feed to the third distillation column 230.

Overhead stream 231 has a temperature at atmospheric pressure from 15 to 100° C., from 20 to 90° C. or from 35 to 75° C. A conventional condenser/cooler may be used to condense the overhead stream 231 to cool the overhead stream 231 to a temperature of not more than 60° C., e.g., not more than 45° C. or not more than 30° C.

In one embodiment, when the extractant 203 is water, the liquid in the bottoms stream 232 contains water as the main component. In addition to the main component, the bottoms stream 232 may contain methyl acetate and lower amounts of acetic acid, methanol, dimethyl ether, methyl iodide, and/or acetaldehyde. This allows a portion of bottoms stream 232 or the whole bottoms stream 232 to be used as the extractant 203 by recycling in line 233 to second distillation column 202. The bottoms stream 232 may have a water mass composition from 85 to 99.99 wt. %, e.g., from 90 to 99.98 wt. % or from 92 to 99 wt. %. Methyl acetate may be retained in the lower part of the third distillation column 230 and is withdrawn in the lower stream 232. The mass composition of methyl acetate in the bottoms stream 232 may be from 0.1 to 15 wt. %, e.g., from 0.5 to 10 wt. %, or from 0.7 to 7 wt. %. The other components, when present, are generally in lower individual amounts of not more than 5 wt. %. In one embodiment, the bottoms stream 232 may have a mass composition of acetaldehyde of not more than 1 wt. %, e.g. not more than 0.5 wt. % or not more than 0.3 wt. %, a mass composition of methyl iodide of not more than 1.5 wt. %, e.g., not more than 1 wt. %, or not more than 0.5 wt. %, a mass composition of acetic acid of not more than 5 wt. %, e.g., not more than 1 wt. %, or not more than 0.5 wt. %, a mass composition of methanol of not more than 1 wt. %, e.g., not more than 0.5 wt. %, or not more than 0.1 wt. %, and/or a mass composition of dimethyl ether of not more than 0.1 wt. %, e.g., not more than 0.01 wt. %, or not more than 0.001 wt. %. Bottoms stream 232 has a temperature at atmospheric pressure from 65 to 165° C., e.g., from 230 to 120° C. or from 85 to 105° C.

Although FIG. 2 shows liquid stream 222 being distilled, in other embodiments, the second mixture 204/204' and/or aqueous stream 215 may be distilled in the third distillation column 230 by without passing through either vessel 214 and/or decanter 220.

Separating methyl iodide from acetaldehyde by distillation alone proves to be unable to fully recover methyl iodide, even though the methyl iodide mass composition is low in overhead stream 231. Further simple distillation may yield marginal or incremental improvements in recovering methyl iodide, thus more effective processing provides attractive benefits for supplemental processing. Extraction with or without distillation may be used as an effective process to enhance recovery of methyl iodide. In one embodiment, a second extractive distillation column may be used to enhance recovery of methyl iodide. As seen in FIG. 2, overhead stream 231 or a distillate portion thereof, is introduced to fourth distillation column 240 that operates as an extractive distillation using a water-containing extractive mixture. Fourth distillation column 240 operates in a manner to obtain an overhead stream 241 enriched in methyl iodide and an aqueous bottom stream 242 enriched in acetaldehyde as well as the extractant, being water. At least a portion, including the entire portion, of aqueous bottom stream 242 may be recycled or returned to second distillation column 202 via line 243 as the extracting mixture.

In one embodiment, the fourth distillation column 240 separates an upper stream 241 from having a ratio (based on weight) of methyl iodide relative to acetaldehyde that is greater than that of the feed in overhead (distillate) stream 231. Upper stream 241 may be taken as an overhead or a stream near the top of fourth distillation column 240. To maintain recovery, it may be useful to direct the upper stream 241, either directly or indirectly, to the reactor 106. In some embodiments, a portion of the upper stream 241 may be introduced to the second distillation column 202, preferably in a lower portion.

For extraction, it is sufficient to add the water-extracting mixture in a counter-current direction at the top of the fourth distillation column 240 via line 244. As described in U.S. Pat. No. 8,859,810, the entire contents and disclosure of which are incorporated by reference, the water-extracting mixture may comprise water, glycols, glycerol, high boiling point alcohols, including mixtures thereof. For the water extractive distillation, the water may have the same temperature as the extractant. The water may be added as a warmed or heated water having the same temperature as the extractant or as a vaporized water (or steam). In one embodiment, the water-extracting mixture 84 has a temperature that is controlled or maintained to be within the range of 0 to 60° C., e.g., 10 to 50° C. or 20 to 40° C. The weight ratio of the flow rate of the water-extracting mixture 244 relative to the flow rate of the overhead stream 231 or a distillate portion thereof [the former/the latter] may range from 1:1000 to 10:1, e.g., from 1:500 to 5:1, 1:100 to 5:1 or 1:4 to 4:1.

In fourth distillation column 240, the overhead stream 241 is cooled and/or condensed, e.g. by passing through a condenser (indirect condenser) and a first portion of the condensate is returned or refluxed to the distillation column 240, while a second portion of the condensate is recycled to the reactor 106 in FIG. 1. Bottom stream 242 is a liquid stream and can be withdrawn in the lower portion of distillation column 240, including the bottom or near the bottom, and contains acetaldehyde and the extractant. Owing to the enriched mass composition of acetaldehyde, liquid stream 242 is purged or discharged outside of the system. A portion of the liquid stream 242 may be used an extractant in either the second distillation column 202 and/or fourth distillation column 240. The overhead stream 241 has a weight ratio of methyl iodide to acetaldehyde that is larger than the methyl iodide to acetaldehyde in liquid stream 242.

The fourth distillation column 240 may have a column top pressure (absolute) from 100 to 500 kPa, e.g., 100 to 400 kPa and 105 to 350 kPa. To effectively separate the overhead, the fourth distillation column 240 at atmospheric pressure has a temperature at the column top from 10 to 90° C., e.g., from 15 to 80° C. or 20 to 60° C., and/or a column bottom temperature from 70 to 170° C., e.g., from 80 to 160° C. or from 90 to 150° C. The number of stages (plates) in the fourth distillation column 240 may be a sufficient number for separation, for example, from 1 to 50 plates, e.g., from 2 to 45 plates or from 3 to 30 plates. The reflux ratio (reflux: distillate) of the fourth distillation column 240 is from 1:20 to 20:1, e.g., from 1:15 to 15:1, or from 5:1 to 10:1.

In one embodiment, the fourth distillation column 240 may have a theoretical stage (or plate) of, for example, less than 50 plates, overhead stream 241 or a condensed portion thereof may have a methyl iodide mass composition from 20 to 80 wt. %, e.g., 30 to 75 wt. % or 40 to 65 wt. %, PRC mass composition from 0.1 to 70 wt. %, e.g., from 0.5 to 65 wt. %, or from 1 to 20 wt. %, methyl acetate mass composition from 0.01 to 15 wt. %, e.g., from 0.05 to 10 wt. %, or from 0.1 to 10 wt. %, acetic acid mass composition from 0 to 5 wt. %, e.g., from 0 to 3 wt. %, or from 0 to 1 wt. %, and water mass composition from 0 to 10 wt. %, from 0 to 8 wt. %, or from 0.01 to 5 wt. %. The mass composition of other organics, such as dimethyl ether and/or methanol, in a mass composition in the overhead stream 241 may be in a minor portion, e.g., not more than 1 wt. % or not more than 0.5 wt. %. Also when the fourth distillation column 240 contains less than 50 plates, the bottom stream 242 may have a PRC mass composition from 1 to 90 wt. %, e.g., from 5 to 80 wt. %, or from 10 to 50 wt. %, water mass composition from 10 to 95 wt. %, from 15 to 90 wt. %, or from 20 to 85 wt. %, methyl iodide mass composition from 0 to 2 wt. %, e.g., 0.01 to 1.5 wt. % or 0.05 to 1 wt. %, methyl acetate mass composition from 0.01 to 15 wt. %, e.g., from 0.05 to 10 wt. %, or from 0.1 to 10 wt. %, acetic acid mass composition from 0 to 5 wt. %, e.g., from 0 to 3 wt. %, or from 0 to 1 wt. %, and a mass composition of organics (dimethyl ether and/or methanol) not more than 3 wt. %, e.g., not more than 1 wt. % or not more than 0.5 wt. %. When the bottom liquid 242 is discharged and/or purged from the process, the acetaldehyde to methyl iodide mass ratio may be from 20:1 to 2000:1, e.g., from 35:1 to 1800:1 or from 50:1 to 1000:1.

In the continuous process to produce acetic acid the process streams, both vapor or liquid streams, may contain various components that are impurities although not described in detail above. These impurities may be formed in the reactor through side reactions. To avoid such impurities it is desirable to suppress the formation of impurities or purge the impurities to prevent build up. The various process stream may contain various amounts formic acid, higher acids, and/or hydrogen iodide.

There may be various configurations of separation process shown in FIG. 2. This includes additional units that supplement or replace the third and/or fourth distillation columns. This allows liquid stream 222 from decanter 220 to bypass third distillation column 230 and is fed into the fourth distillation column 240 or may be fed to one or more extraction vessels. Thus, if necessary, acetaldehyde may be extracted with water from the liquid stream 222 by one or a plurality of water extraction vessel that are provided with a mixer and a settler or by the fourth distillation column 240. In other embodiments, it may not be necessary to use third and/or fourth distillation columns to purify liquid stream 222.

FIG. 3 illustrates another embodiment of an acetaldehyde or PRC removal system 200. In one embodiment, feed composition in line 201 introduced to the second distillation column 202 has the lower phase from the condensed overhead in FIG. 1. This allows feed composition in line 201 to contain $C_1$-$C_{12}$ alkyl iodides (mainly represented by methyl iodide) in an amount from 60 to 98 wt. %, e.g., from 60 to 95 wt. % or from 75 to 93 wt. %, PRC (acetaldehyde) in an amount of up to 5 wt. %, e.g., up to 3 wt. % or up to 0.5 wt. %, and water in an amount up to 3 wt. %, e.g., up to 1 wt. % or up to 0.8 wt. %. Further, feed line also contains low amounts of methanol and if the methanol needs to be adjusted feed line can be made to comprise a portion of upper phase. As described above, an extractant is added via line 203 above the collector tray 205. Any vapors at the top are collected, condensed and refluxed to the second distillation column 202.

In this embodiment, sidestream 204' is condensed or chilled, from −5° C. to 60° C., for direct feeding to decanter 220, thus skipping vessel 214 in FIG. 2, for liquid-liquid separation to obtain a residual stream 221 (containing methyl iodide) and a liquid stream 222 (containing acetaldehyde). The mass flow ratio of the liquid stream 222 and the residual stream 221 may be from 1:500 to 1:0.5 (liquid to residual), e.g., from 1:400 to 1:1 or from 1:375 to 1:10. Sidestream may have a composition is suitable of phase separation and in one embodiment, the composition of the sidestream 204' may have a PRC mass composition from 0.1 to 90 wt. %, e.g., from 0.2 to 65 wt. % or from 0.5 to 50 wt. %, $C_1$-$C_{12}$ alkyl iodides (methyl iodide) mass composition from 0.5 to 95 wt. %, e.g., from 1 to 95 wt. %, from 5 to 90 wt. %, or from 10 to 60 wt. %, methyl acetate mass composition from 0.1 to 25 wt. %, e.g., from 0.5 to 20 wt. %, or from 0.5 to 10 wt. %, acetic acid mass composition from 0 to 10 wt. %, e.g., from 0.01 to 5 wt. %, or from 0.05 to 1 wt. %, water mass composition from 0.1 to 20 wt. %, e.g., from 0.5 to 15 wt. %, or from 0.5 to 8 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. The process as shown in FIG. 3 further concentrates the PRC without building up large quantities of acetals.

As shown in FIG. 3, residual stream 221 combined with the lower stream 206 from the second distillation column 202. In some embodiments, residual stream 221 may be fed to the lower portion of the second distillation column 202.

Acetic acid, as a miscible solvent, was fed via a feed line 203' to the lower portion of second distillation column 202, and may in some embodiments be fed below the feed location of stream 203. Although not shown in FIG. 3, there may be a miscible solvent fed to the second distillation column 202.

Once withdrawn from decanter 220, liquid stream 222 is fed to the third distillation column 230. Despite the smaller relative stream, the liquid stream 222 contains an useful amount of acetaldehyde. The acetaldehyde mass composition in liquid stream 222 based on amount may be more than 2× the amount in residual stream 221, e.g., more than 3× or more than 4×. As described above, third distillation column 230 operates to yield an overhead stream 231 containing acetaldehyde in an amount from 1 to 99 wt. % and methyl iodide in an amount from 0.1 to 30 wt. %, and a bottoms stream 232 containing the extractant as the main component in an amount of not less than 10 wt. %, and methyl iodide in an amount of not more than 1 wt. % (provided that, each stream, including impurities, has a total amount of 100% by weight). A portion of the bottoms stream 232 may be used as the extractant and returned to second distillation column 202. In other embodiment, bottoms stream 232 may be removed or discharged from the process.

The overhead stream 231 or a distillate thereof contain more acetaldehyde and has a lower methyl iodide mass composition than second mixture. In one embodiment, the composition of overhead stream 231 comprises a PRC (acetaldehyde) mass composition from 45 to 99 wt. %, e.g., from 50 to 99 wt. % or from 60 to 98 wt. %, $C_1$-$C_{12}$ alkyl iodides (methyl iodide) mass composition from 0.1 to 30 wt. %, e.g., from 0.5 to 25 wt. %, or from 1 to 20 wt. %, methyl acetate mass composition from 0.1 to 25 wt. %, e.g., from 0.5 to 20 wt. %, or from 0.5 to 12 wt. %, acetic acid mass composition from 0 to 5 wt. %, e.g., from 0 to 1.5 wt. %, or from 0 to 1 wt. %, water mass composition from 0 to 5 wt. %, e.g., from 0 to 2.5 wt. %, or from 0.01 to 2 wt. %, methanol mass composition from 0 to 2.5 wt. %, e.g., from 0.01 to 2.1 wt. %, or from 0.05 to 2 wt. %, acetal mass composition from 0 to 2.5 wt. %, e.g., from 0.01 to 1.7 wt. %, or from 0.05 to 1.5 wt. %, and dimethyl ether mass composition from 0 to 1.2 wt. %, e.g., from 0.01 to 0.8 wt. %, or from 0.05 to 0.5 wt. %. In one embodiment, the overhead stream 231 has a ratio (based on weight) of methyl iodide relative to acetic acid is that higher than this ratio in feed to the third distillation column 230. In addition or separately, the overhead stream 231 may have a ratio (based on weight) of methyl iodide relative to methyl acetate is that higher than this ratio in feed to the third distillation column 230. The bottoms stream 232 may have a water mass composition from 85 to 99.99 wt. %, e.g., from 90 to 99.98 wt. % or from 92 to 99 wt. %. In one embodiment, bottoms stream 232 is removed from the process or at least a portion thereof may be returned as the extractant to the second distillation column 202.

Similar to the previous figures, FIG. 3 processes the overhead stream 231 or a distillate portion thereof, by introducing this stream to the fourth distillation column 240 that operates as an extractive distillation using a water-containing extractive mixture. As described above, fourth distillation column 240 operates in a manner with an water-extracting mixture via line 244 to obtain an overhead stream 241 enriched in methyl iodide and an aqueous bottom stream 242 enriched in acetaldehyde as well as the extractant, being water. At least a portion, including the entire portion, of aqueous bottom stream 242 may be recycled or returned to second distillation column 202 via line 243 as the extracting mixture.

Subsequent Treatment Steps

As noted above, the process described herein includes one or more subsequent purification steps for purifying or improving the quality (purity) of acetic acid. These are In some embodiments, the side stream 144 of the first distillation column 140 is subjected to further purification. For example, acetic acid removed via side stream 144 may be subjected to further distillation, such as in a dehydrating column 180. The dehydrating column 180 separates the side stream 144 to form an overhead stream 182 comprised primarily of water and an acetic acid product stream 184, 184' comprised primarily of acetic acid. The overhead stream 182 may comprise water in an amount of 25 wt. % or more, e.g., 30 wt. % or more or 50 wt. % or more. In one embodiment, the overhead stream 182 may comprise water in an amount from 50 to 75 wt. %. Methyl acetate and methyl iodide are also removed from the side stream and concentrated in the overhead stream 182. The acetic acid product stream 184, 184' preferably comprises or consists essentially of acetic acid. In preferred embodiments, the acetic acid product stream 184, 184' comprises acetic acid in an amount greater than or equal to 90 wt. %, e.g., greater than or equal to 95 wt. % or greater than or equal to 98 wt. %. Furthermore, in preferred embodiments, the acetic acid product stream 184, 184' comprises less than or equal to 0.2 wt. % water, e.g., less than or equal to 0.15 wt. % water.

The overhead stream 182 from the dehydrating column 180 may contain a reaction component, such as methyl iodide, methyl acetate, and water, and it is preferable to retain these reaction components within the process. In order to do so, the overhead stream 182 may be condensed, e.g. by a heat exchanger, and recycled to the reactor 106 and/or refluxed to the dehydrating column 180. In one embodiment, the overhead stream 182 (or a condensed portion thereof) is refluxed to the dehydrating column 180 at a reflux ratio from 0.2 to 15, wherein the reflux ratio is the amount of the overhead stream reflux/the amount of the overhead stream distilled. An off-gas component may be vented from the condensed overhead stream 182. Similar to the condensed low-boiling overhead vapor stream, the condensed overhead stream of the dehydrating column 180 may also be separated to form an aqueous phase and an organic phase, and these phases may be recycled or refluxed as needed to maintain the amounts in the reaction medium.

The acetic acid product stream is preferably a lower stream from the dehydrating column. In some embodiments of the process, the acetic acid product stream is a bottom stream 184 of the dehydrating column, a lower side stream of the dehydrating column, or a combination thereof.

As noted above, the acetic acid product stream 184, 184' comprises the product acetic acid. Preferably, the acetic acid product stream 184, 184' has a higher amount of acetic acid than the side stream (crude acetic acid stream) 144. Nevertheless, the acetic acid product stream may comprise small amounts of impurities, e.g., 1,1-dimethoxyethane. The mass composition of 1,1-dimethoxyethane in the acetic acid product stream may be less than 0.2 wt. %, e.g., less than 0.15 wt. %, less than 0.1 wt. %, or less than 0.05 wt. %. Because the acetic acid product stream may comprise 1,1-dimethoxy-ethane, it is preferred that no stream comprising air or oxygen be allowed to contact the acetic acid product stream, so as to reduce the risk of oxidation.

The acetic acid product stream 184, 184' may be further processed, e.g., by removing higher boiling components. In some embodiments, the higher boiling components by subjecting the acetic acid product stream to further distillation, such as in a heavy ends removal column (finishing column) 190. The heavy ends removal column separates the acetic acid product stream 184 into a heavy ends stream 194 as the bottoms stream. A vent gas 192 may be removed as a an off-gas and subject to further treatment, e.g., in a scrubber system. A purified acetic acid product stream 196 may be removed as a side stream of the heavy ends removal column 190 and subjected to further treatment.

The acetic acid product stream 184' and/or the purified acetic acid product stream 196 may be further processed, e.g., by passing through an ion exchange resin 198, prior to being stored or transported for commercial use. Carboxylic acid streams, e.g., acetic acid streams, that are contaminated with halides and/or corrosion metals may be contacted with the ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615, 806; 5,653,853; 5,731,252; and 6,225,498, which are hereby incorporated by reference in their entireties. Generally, a contaminated liquid carboxylic acid stream is contacted with an ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, due to the presence of lithium acetate in the reaction medium, there may be some undesirable carryover of lithium. Without being bound by theory, lithium derived from the lithium acetate in the reaction may carry over in the acetic acid product. Lithium may cause displacement having metal-exchanged strong acid cation site. By using a cation exchanger to remove lithium prior to the use of a resin having metal-exchanged strong acid cation sites, the displacement of silver, mercury, palladium and/or rhodium from the metal-exchanged sites by the lithium is reduced or eliminated. According to one embodiment, the lithium, and preferably lithium cation, is removed prior to the iodide removal to prevent displacement in the metal ion-exchange resin.

Lithium has also been found to be entrained in the crude acid product in the absence of heavy ends and other finishing apparatus. Even in very small amounts of 10 wppb of lithium in the crude acid product may cause problem for displacing metal-exchanged resin. The lithium in the acid-containing crude acid product exiting the dehydrating column of an acetic acid process, e.g., the last column in the primary purification train, may be in an amount up to or equal to 10 wppm of lithium, e.g., up to or equal to 5 wppm, up to or equal to 1 wppm, up to or equal to 500 wppb, up to or equal to 300 wppb, or up to or equal to 100 wppb. In terms of ranges, the crude acid product may comprise lithium in an amount from 0.01 wppm to 10 wppm, e.g., from 0.05 wppm to 5 wppm or from 0.05 wppm to 1 wppm. By utilizing a cationic exchanger in the acid form before introducing the crude acid product to a metal-exchanged resin, significant amounts of lithium can be removed. For example greater than or equal to 90 wt. % of the lithium in the stream might be removed by the cationic exchanger, e.g., 95 wt. % or 99 wt. %. Thus, the stream exiting the acid-form cationic exchanger may contain less than or equal to 50 wppb lithium, e.g., less than or equal to 10 wppb, or less than or equal to 5 wppb. Such removal of the lithium can greatly extend the life of the metal-exchanged resin.

The configuration of the guard bed within an acetic acid purification train may vary widely. For example, the guard bed may be configured after a dehydrating column. Additionally or alternatively, the guard be may be configured after a heavy ends removal column (finishing column). In the embodiment shown in FIG. 1, for example, the acetic acid product stream 184' and the purified acetic acid product stream 196 of the heavy ends removal column 190 is withdrawn and subjected to treatment in the guard bed 198. Preferably the guard bed is configured in a position wherein the temperature acetic acid product stream is low, e.g., less than or equal to 120° C. or less than or equal to 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used. A final product stream 199 is then removed from the guard bed 198.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide mass composition, in one embodiment the purified acetic acid product in bottoms stream 127 is contacted with a guard bed when total iodide mass composition of the purified acetic acid product is less than or equal to 1 wppm. Total iodide mass composition includes iodide from both organic sources, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than or equal to 100 wppb iodides, e.g., less than or equal to 90 wppb, less than or equal to 50 wppb, or less than or equal to 25 wppb. In one embodiment, the purified acetic acid composition comprises less than or equal to 1000 wppb corrosion metals, e.g., less than or equal to 750 wppb, less than or equal to 500 wppb, or less than or equal to 250 wppb. For purposes of the present invention, corrosion metals include metals selected from the group consisting of nickel, iron, chromium, molybdenum and combinations thereof. In terms of ranges, the purified acetic acid composition may comprise from 0 to 100 wppb iodides, e.g., from 1 to 50 wppb, and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

As noted above, off-gas streams may be vented during various steps of the process, e.g., the reaction step, the phase separation step, and/or the purifying step. These vent streams, in particular lines 108, 112, 170, 182, and 192 of FIG. 1, may contain residue organics and iodides. To recover these valuable components, these lines may be fed to a scrubber 114 that operates, e.g., with an absorption solvent (scrubbing solvent) 115, such as acetic acid, methanol, methyl acetate, and combinations thereof, to remove methyl acetate and methyl iodide. A suitable scrubber is described in U.S. Pat. No. 8,318,977, which is incorporated herein by reference in its entirety. As described therein, the off-gas treatment step may comprise multiple absorbing steps, e.g., with differing absorption solvents and/or differing pressures. For example, a vent stream may be introduced to an absorber tower to recover any remaining useful components, such as carbon monoxide, methyl acetate and/or methyl iodide in line. The tower may operate at a pressure of greater than or equal to 0.7 atm (gauge), e.g., greater than or equal to 1 atm or greater than or equal to 2 atm. The separation and recovery in the absorber tower may be performed according to a wet process using an absorbing liquid, such as water, acetic acid, methyl acetate or methanol. A crude acetic acid product may be used as the absorption solvent 115. This wet process removes substantially all of the remaining methyl iodide present in the gaseous portion and recovers methyl iodide by absorption into the absorbing liquid. A vent purge (gaseous component) 116 may be removed (diffused) from the top of the absorbing tower. Meanwhile, a second vent stream may continue to the same or another pressure absorber tower (not shown) to recover any remaining useful components, such as carbon monoxide, methyl acetate and/ or methyl iodide in line. Methyl iodide, hydrogen iodide, and other condensable gaseous components in the second vent stream may be absorbed by an absorbing liquid (absor-bent) in the same or another absorber tower. A second vent purge (gaseous component) may be removed (diffused) from the absorption column with the first absorption solvent at a first pressure and/or from the absorption column with the second absorption solvent at the second pressure, lower than the first pressure.

The distillation columns described herein may be con-ventional distillation columns, e.g., a plate column, a packed column, and others, and combinations thereof. Plate col-umns may include a perforated plate column, bubble-cap column, Kittel tray column, uniflux tray, or a ripple tray column. For a plate column, the theoretical number of plates is not particularly limited and depending on the species of the component to be separated, may include up to 80 plates, e.g., from 2 to 80, from 5 to 60, from 5 to 50, or more preferably from 7 to 35. The distillation column may include a combination of different distillation apparatuses. Unless excluded, a combination of bubble-cap column and perfo-rated plate column may be used, as well as a combination of perforated plate column and a packed column.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molyb-denum and others. Suitable nickel-based alloys include those containing nickel as a main component and one or more of chromium, iron, cobalt, molybdenum, tungsten, manganese, and others, e.g., HASTELLOY™ and INC-ONEL™. Corrosion-resistant metals may be particularly suitable as materials for the distillation system and various lines.

At the outset, it should be noted that in the development of any such actual embodiment, numerous implementation-specific decisions must be made to achieve the developer's specific goals, such as compliance with system related and business related constraints, which will vary from one implementation to another. In addition, the processes dis-closed herein can also comprise components other than those cited or specifically referred to, as is apparent to one having average or reasonable skill in the art.

As is evident from the figures and text presented above, a variety of embodiments are contemplated.

The present invention will be better understood in view of the following non-limiting examples.

EXAMPLES

The present invention will be better understood in view of the following non-limiting examples.

In Example 1, a semi-empirical simulator was used to study the effect of methanol mass composition on the formation of 1,1-dimethoxyethane. Tests assessed the effect of methanol mass composition on the mass composition of 1,1-dimethoxyethane in the lower stream (residue stream) of an experimental second distillation column. In these tests, three different samples of a lower phase from the receiver were fed to the second distillation column of the second distillation step. The second distillation column had a col-umn top temperature of 37° C., a column bottom tempera-ture of 44° C., and a column top pressure of 1.01 atm. The extractive distillation had 45 plates. The extractant was a water-containing stream and the extractant was fed to the top plate. The extractant did not contain methanol and no other sources of methanol were fed to the extractive distillation column other than the first mixture. The temperature of the extractant was 20° C. Results of these examples are show in Table 3.

TABLE 3

| | Composition of Second Distillation Column Streams (wt. %) | | | | | |
| | Example 1 | | Example 2 | | Example 3 | |
| | INLET | RESIDUE | INLET | RESIDUE | INLET | RESIDUE |
|---|---|---|---|---|---|---|
| Methyl Iodide | 80.04 | 76.37 | 82.5 | 85.88 | 82.5 | 78.2 |
| Methyl Acetate | 14.77 | 19.52 | 14.8 | 16.28 | 14.78 | 19.17 |
| Acetic Acid | 1.83 | 2.98 | 1.83 | 2.2 | 1.83 | 2.51 |
| Acetaldehyde | 0.196 | 0.02 | 0.196 | 0.0048 | 0.196 | 0.02 |

TABLE 3-continued

| | Example 1 | | Example 2 | | Example 3 | |
|---|---|---|---|---|---|---|
| | INLET | RESIDUE | INLET | RESIDUE | INLET | RESIDUE |
| Methanol | 2.518 | 0.81 | 0.1128 | 0.036 | 0.0033 | 0 |
| Water | 0.7 | 0.18 | 0.701 | 0.488 | 0.70 | 0.1 |
| 1,1-dimethoxyethane | 0 | 0.11 | 0 | 0.0172 | 0 | 0 |

Composition of Second Distillation Column Streams (wt. %)

Each run operated with a first mixture in the inlet having a mass ratio of methyl iodide to water than was greater than 1. In addition, the liquid stream in the residue also had a mass ratio of methyl iodide to water than being greater than 1, e.g., 424 (Example 1), 175 (Example 2), and 782 (Example 3).

From the results of Example 1, it is evident that as the charging mixture has a lower mass composition of methanol, the mass composition of 1,1-dimethoxyethane in the bottom stream (residue stream) of the second distillation column decreases.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EMBODIMENTS

As used below, any reference to a series of embodiments is to be understood as a reference to each of those embodiments disjunctively (e.g., "Embodiments 1-4" is to be understood as "Embodiments 1, 2, 3, or 4").

Embodiment 1 is a process for producing acetic acid, comprising: (a) a reaction step of allowing methanol to continuously react with carbon monoxide in a reactor in the presence of a reactive system comprising a metal catalyst, an ionic metal iodide, and methyl iodide, acetic acid, methyl acetate, and water; (b) an evaporation step of separating a reaction mixture obtained in the reaction step with or without heating into a vapor stream and a liquid residuum stream; (c) a first distillation step of distilling at least a portion of the vapor stream in a first distillation column to form a first overhead stream and a side stream, wherein the first overhead stream comprises water, methyl iodide, and/or acetaldehyde, and the side stream comprises acetic acid; (d) a phase separation step of condensing the first overhead stream in one or more condensers, collecting the condensates in a receiver, and separating the condensates into an upper phase and a lower phase; (e) a second distillation step of distilling at least a portion of the lower phase in a second distillation column to form a second mixture comprising acetaldehyde; (f) an acetaldehyde separation step of separating the second mixture into an acetaldehyde stream and a first return stream; and at least one step selected from the group consisting of (g) to (k): (g) a purifying step of purifying the side stream to obtain an acetic acid product stream; (h) an off-gas treatment step of absorbing one or more off-gas streams from the process with an absorption solvent and forming a carbon monoxide stream and a second return stream; (i) a high-boiler removal step of removing a higher boiling component from the acetic acid product stream; (j) an iodine removal step of contacting the acetic acid product stream with an ion-exchange resin and separating an iodine compound from the acetic acid product stream; and (k) an extraction step of extracting acetaldehyde from the acetaldehyde stream to form an extract and a raffinate, wherein the extract comprises acetaldehyde and the raffinate comprises methyl iodide; wherein the mass composition of 1,1-dimethoxyethane in a liquid stream of the process is controlled to be not more than 0.2 wt. %.

Embodiment 2 is the process of embodiment(s) 1, wherein the liquid stream contains at least one member selected from the group consisting of methyl iodide, methyl acetate, and water.

Embodiment 3 is the process of embodiment(s) 1-2, wherein the liquid stream has a mass ratio of methyl iodide to water that is greater than 1.

Embodiment 4 is the process of embodiment(s) 1-3, wherein no stream comprising air or oxygen is contacted with the liquid stream.

Embodiment 5 is the process of embodiment(s) 1-4, wherein the mass composition of 1,1-dimethoxyethane in the liquid stream is controlled to be not more than 0.2 wt. % by controlling a methanol mass composition in the first overhead stream.

Embodiment 6 is the process of embodiment(s) 1-5, wherein the mass composition of 1,1-dimethoxyethane in the liquid stream is controlled to be not more than 0.2 wt. % by controlling a residence time in the first distillation column and/or the second distillation column to be not less than 1 minute.

Embodiment 7 is the process of embodiment(s) 1-6, wherein the mass composition of the 1,1-dimethoxyethane in the liquid stream is controlled to be from 0.01 to 0.2 wt. %.

Embodiment 8 is the process of embodiment(s) 1-7, wherein the mass composition of the 1,1-dimethoxyethane in the liquid stream is controlled to be not more than 0.1 wt. %.

Embodiment 9 is the process of embodiment(s) 1-8, wherein the liquid stream is selected from the side stream, the bottom streams, the condensates, the upper phase, the lower phase, the second mixture, and/or the acetic acid product stream.

Embodiment 10 is the process of embodiment(s) 1-9, wherein the weight ratio of methyl iodide to water in the lower phase is greater than 1.

Embodiment 11 is the process of embodiment(s) 1-10, wherein the second mixture is an overhead stream and/or a side cut stream of the second distillation column.

Embodiment 12 is the process of embodiment(s) 1-11, wherein the upper phase is refluxed to the first distillation column at a reflux ratio from 0.5 to 20, wherein the reflux ratio is the amount of the upper phase refluxed/the amount of upper phase distilled.

Embodiment 13 is the process of embodiment(s) 1-12, wherein an overhead of the second distillation column is refluxed to the second distillation column at a reflux ratio from 0.2 to 15, wherein the reflux ratio is the amount of the overhead refluxed/the amount of overhead distilled.

Embodiment 14 is the process of embodiment(s) 1-13, wherein the second mixture comprises less than or equal to 2 wt. % methanol.

Embodiment 15 is the process of embodiment(s) 1-14, wherein the purifying step comprises at least one step selected from the group consisting of steps (l)-(n): (l) feeding the side stream to a dehydrating column to yield an overhead stream and a bottom stream comprising the acetic acid product; (m) feeding the side stream to a dehydrating column to yield an overhead stream and a lower side cut stream comprising the acetic acid product; (n) feeding the side stream to a dehydrating column to yield an overhead stream comprising water in an amount of 25 wt. % or more, and a lower stream comprising water in an amount of less than or equal to 0.2 wt. %.

Embodiment 16 is the process of embodiment(s) 15, wherein the overhead stream is refluxed to the dehydrating column at a reflux ratio from 0.2 to 15, wherein the reflux ratio is the amount of the overhead stream reflux/the amount of the overhead stream distilled.

Embodiment 17 is the process according to claim 1-16, wherein the off-gas treatment step comprises at least one step selected from the group consisting of steps (o)-(q): (o) absorbing the off-gas streams with a first absorption solvent selected from the group consisting of acetic acid, methanol, methyl acetate and combinations thereof, at a first pressure; (p) absorbing the off-gas streams with a second absorption solvent selected from the group consisting of acetic acid, methanol, methyl acetate and combinations thereof, at a second pressure, wherein the second pressure is lower than the first pressure; and (q) diffusing a gaseous component absorbed in the steps (o) and/or (p).

Embodiment 18 is the process of embodiment(s) 1-17, wherein the higher boiling component comprises propionic acid, butyl acetate, 2-ethyl crotonaldehyde, or mixtures thereof.

Embodiment 19 is the process of embodiment(s) 1-18, further comprising maintaining a hydrogen partial pressure of from 0.3 to 2 atm in the reactor by introducing a hydrogen-containing stream into the reactor.

Embodiment 20 is the process of embodiment(s) 1-19, wherein the acetaldehyde separation step comprises separating the second mixture in one or more extractors and/or one or more additional distillation columns.

We claim:

1. A process for producing acetic acid, comprising:
    (a) a reaction step of allowing methanol to continuously react with carbon monoxide in a reactor in the presence of a reactive system comprising a metal catalyst, an ionic metal iodide, and methyl iodide, acetic acid, methyl acetate, and water;

(b) an evaporation step of separating a reaction mixture obtained in the reaction step with or without heating into a vapor stream and a liquid residuum stream;
    (c) a first distillation step of distilling at least a portion of the vapor stream in a first distillation column to form a first overhead stream and a side stream, wherein the first overhead stream comprises water, methyl iodide, and/or acetaldehyde, and the side stream comprises acetic acid;
    (d) a phase separation step of condensing the first overhead stream in one or more condensers, collecting condensates in a receiver, and separating the condensates into an upper phase and a lower phase;
    (e) a second distillation step of distilling at least a portion of the lower phase in a second distillation column to form a second mixture comprising acetaldehyde;
    (f) an acetaldehyde separation step of separating the second mixture into an acetaldehyde stream and a first return stream;
    and at least one step selected from the group consisting of (g) to (k):
    (g) a purifying step of purifying the side stream to obtain an acetic acid product stream;
    (h) an off-gas treatment step of absorbing one or more off-gas streams from the process with an absorption solvent and forming a carbon monoxide stream and a second return stream;
    (i) a high-boiler removal step of removing a higher boiling component from the acetic acid product stream;
    (j) an iodine removal step of contacting the acetic acid product stream with an ion-exchange resin and separating an iodine compound from the acetic acid product stream; and
    (k) an extraction step of extracting acetaldehyde from the acetaldehyde stream to form an extract and a raffinate, wherein the extract comprises acetaldehyde and the raffinate comprises methyl iodide;
    wherein the mass composition of 1,1-dimethoxyethane in a liquid stream of the process is controlled to be not more than 0.2 wt. % by maintaining the amount of unreacted methanol in the reaction mixture to less than 1 wt. % based on the total weight of the reaction mixture.

2. The process of claim 1, wherein the liquid stream contains at least one member selected from the group consisting of methyl iodide, methyl acetate, and water.

3. The process of claim 1, wherein the liquid stream has a mass ratio of methyl iodide to water that is greater than 1.

4. The process of claim 1, wherein no stream comprising air or oxygen is contacted with the liquid stream.

5. The process of claim 1, wherein the mass composition of 1,1-dimethoxyethane in the liquid stream is further controlled to be not more than 0.2 wt. % by controlling a methanol mass composition in the first overhead stream.

6. The process of claim 1, wherein the mass composition of 1,1-dimethoxyethane in the liquid stream is further controlled to be not more than 0.2 wt. % by controlling a residence time in the first distillation column and/or the second distillation column to be not less than 1 minute.

7. The process of claim 1, wherein the mass composition of the 1,1-dimethoxyethane in the liquid stream is controlled to be from 0.01 to 0.2 wt. %.

8. The process of claim 1, wherein the mass composition of the 1,1-dimethoxyethane in the liquid stream is controlled to be not more than 0.1 wt. %.

9. The process of claim 1, wherein the liquid stream is selected from the side stream, the condensates, the upper phase, the lower phase, the second mixture, and/or the acetic acid product stream.

10. The process of claim 1, wherein the weight ratio of methyl iodide to water in the lower phase is greater than 1.

11. The process of claim 1, wherein the second mixture is an overhead stream and/or a side cut stream of the second distillation column.

12. The process of claim 1, wherein the upper phase is refluxed to the first distillation column at a reflux ratio from 0.5 to 20, wherein the reflux ratio is the amount of the upper phase refluxed/the amount of upper phase distilled.

13. The process of claim 1, wherein an overhead of the second distillation column is refluxed to the second distillation column at a reflux ratio from 0.2 to 15, wherein the reflux ratio is the amount of the overhead refluxed/the amount of overhead distilled.

14. The process of claim 1, wherein the second mixture comprises less than or equal to 2 wt. % methanol.

15. The process of claim 1, wherein the purifying step comprises at least one step selected from the group consisting of steps (l)-(n):

(l) feeding the side stream to a dehydrating column to yield an overhead stream and a bottom stream comprising the acetic acid product;

(m) feeding the side stream to a dehydrating column to yield an overhead stream and a lower side cut stream comprising the acetic acid product;

(n) feeding the side stream to a dehydrating column to yield an overhead stream comprising water in an amount of 25 wt. % or more, and a lower stream comprising water in an amount of less than or equal to 0.2 wt. %.

16. The process of claim 15, wherein the overhead stream is refluxed to the dehydrating column at a reflux ratio from 0.2 to 15, wherein the reflux ratio is the amount of the overhead stream reflux/the amount of the overhead stream distilled.

17. The process according to claim 1, wherein the off-gas treatment step comprises at least one step selected from the group consisting of steps (o)-(q):

(o) absorbing the off-gas streams with a first absorption solvent selected from the group consisting of acetic acid, methanol, methyl acetate and combinations thereof, at a first pressure;

(p) absorbing the off-gas streams with a second absorption solvent selected from the group consisting of acetic acid, methanol, methyl acetate and combinations thereof, at a second pressure, wherein the second pressure is lower than the first pressure; and (q) diffusing a gaseous component absorbed in the steps (o) and/or (p).

18. The process of claim 1, wherein the higher boiling component comprises propionic acid, butyl acetate, 2-ethyl crotonaldehyde, or mixtures thereof.

19. The process of claim 1, further comprising maintaining a hydrogen partial pressure of from 0.3 to 2 atm in the reactor by introducing a hydrogen-containing stream into the reactor.

20. The process of claim 1, wherein the acetaldehyde separation step comprises separating the second mixture in one or more extractors and/or one or more additional distillation columns.

* * * * *